(12) United States Patent
Heartlein et al.

(10) Patent No.: US 10,087,247 B2
(45) Date of Patent: Oct. 2, 2018

(54) METHODS AND COMPOSITIONS FOR DELIVERING MRNA CODED ANTIBODIES

(71) Applicant: TRANSLATE BIO, INC., Cambridge, MA (US)

(72) Inventors: Michael Heartlein, Cambridge, MA (US); Frank Derosa, Cambridge, MA (US); Anusha Dias, Cambridge, MA (US); Braydon Charles Guild, Concord, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 14/775,835

(22) PCT Filed: Mar. 14, 2014

(86) PCT No.: PCT/US2014/027717
§ 371 (c)(1),
(2) Date: Sep. 14, 2015

(87) PCT Pub. No.: WO2014/152774
PCT Pub. Date: Sep. 25, 2014

(65) Prior Publication Data
US 2016/0031981 A1    Feb. 4, 2016

Related U.S. Application Data

(60) Provisional application No. 61/920,165, filed on Dec. 23, 2013, provisional application No. 61/784,903, filed on Mar. 14, 2013.

(51) Int. Cl.
| | |
|---|---|
| *C07K 16/24* | (2006.01) |
| *C07K 16/22* | (2006.01) |
| *C12N 15/88* | (2006.01) |
| *A61K 9/00* | (2006.01) |
| *A61K 9/127* | (2006.01) |
| *A61K 47/69* | (2017.01) |

(52) U.S. Cl.
CPC ............ *C07K 16/24* (2013.01); *A61K 9/0019* (2013.01); *A61K 9/127* (2013.01); *A61K 9/1271* (2013.01); *A61K 9/1272* (2013.01); *A61K 47/6911* (2017.08); *C07K 16/22* (2013.01); *C12N 15/88* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 5,705,385 A | 1/1998 | Bally et al. | |
| 5,976,567 A | 11/1999 | Wheeler | |
| 5,981,501 A | 11/1999 | Wheeler et al. | |
| 6,534,484 B1 | 3/2003 | Wheeler et al. | |
| 6,815,432 B2 | 11/2004 | Wheeler et al. | |
| 7,422,902 B1 | 9/2008 | Wheeler et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,901,708 B2 | 3/2011 | MacLachlan et al. | |
| 8,101,741 B2 | 1/2012 | MacLachlan et al. | |
| 8,188,263 B2 | 5/2012 | MacLachlan et al. | |
| 8,236,943 B2 | 8/2012 | Lee et al. | |
| 8,329,070 B2 | 12/2012 | MacLachlan et al. | |
| 8,513,403 B2 | 8/2013 | MacLachlan et al. | |
| 8,569,256 B2 | 10/2013 | Heyes et al. | |
| 8,710,200 B2 | 4/2014 | Schrum et al. | |
| 8,822,663 B2 | 9/2014 | Schrum et al. | |
| 8,883,202 B2 | 11/2014 | Manoharan et al. | |
| 8,980,864 B2 | 3/2015 | Hoge et al. | |
| 9,051,567 B2 | 6/2015 | Fitzgerald et al. | |
| 9,061,059 B2 | 6/2015 | Chakraborty et al. | |
| 9,089,604 B2 | 7/2015 | Chakraborty et al. | |
| 9,095,552 B2 | 8/2015 | Chakraborty et al. | |
| 9,107,886 B2 | 8/2015 | Chakraborty et al. | |
| 9,114,113 B2 | 8/2015 | Chakraborty et al. | |
| 9,181,319 B2 | 11/2015 | Schrum et al. | |
| 9,186,325 B2 | 11/2015 | Manoharan et al. | |
| 9,186,372 B2 | 11/2015 | de Fougerolles et al. | |
| 9,187,748 B2 | 11/2015 | Geisbert et al. | |
| 9,192,651 B2 | 11/2015 | Chakraborty et al. | |
| 9,220,755 B2 | 12/2015 | Chakraborty et al. | |
| 9,220,792 B2 | 12/2015 | Chakraborty et al. | |
| 9,233,141 B2 | 1/2016 | Chakraborty et al. | |
| 9,254,311 B2 | 2/2016 | Bancel et al. | |
| 9,295,689 B2 | 3/2016 | de Fougerolles et al. | |
| 9,301,993 B2 | 4/2016 | Chakraborty et al. | |
| 9,303,079 B2 | 4/2016 | Chakraborty et al. | |

(Continued)

FOREIGN PATENT DOCUMENTS

| | | |
|---|---|---|
| CA | 2807 552 | 9/2012 |
| EP | 1519 714 | 10/2010 |

(Continued)

OTHER PUBLICATIONS

Ho, S. et al., "IRES-mediated Tricistronic vectors for enhancing generation of high monoclonal antibody expressing CHO cell lines", J. Biotech., Oct. 2011, vol. 157: pp. 130-139.*

(Continued)

*Primary Examiner* — Michael D Burkhart
(74) *Attorney, Agent, or Firm* — Proskauer Rose LLP; Fangli Chen; Sanjukta Ghosh

(57) ABSTRACT

The present invention provides, among other things, methods and compositions for delivering an antibody in vivo by administering to a subject in need thereof one or more mRNAs encoding a heavy chain and a light chain of an antibody, and wherein the antibody is expressed systemically in the subject. In some embodiments, the one or more mRNAs comprise a first mRNA encoding the heavy chain and a second mRNA encoding the light chain of the antibody.

17 Claims, 7 Drawing Sheets

Specification includes a Sequence Listing.

(56) References Cited

U.S. PATENT DOCUMENTS

| | | | |
|---|---|---|---|
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,535 B2 | 8/2016 | de Fougerolles et al. |
| 9,428,751 B2 | 8/2016 | MacDonald et al. |
| 9,447,164 B2 | 9/2016 | Schrum et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworksi et al. |
| 9,572,874 B2 | 2/2017 | Fotin-Mleczek et al. |
| 9,572,896 B2 | 2/2017 | Bancel et al. |
| 9,572,897 B2 | 2/2017 | Bancel et al. |
| 9,587,003 B2 | 3/2017 | Bancel et al. |
| 9,616,084 B2 | 4/2017 | Mutzke |
| 9,623,095 B2 | 4/2017 | Kallen et al. |
| D787,703 S | 5/2017 | Mayer |
| 9,636,301 B2 | 5/2017 | Weber |
| 9,655,955 B2 | 5/2017 | Hoerr et al. |
| 9,657,295 B2 | 5/2017 | Schrum et al. |
| 9,669,089 B2 | 6/2017 | Thess et al. |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2008/0145413 A1* | 6/2008 | Panzner ............... A61K 9/1272 424/450 |
| 2009/0270481 A1 | 10/2009 | MacLachlan et al. |
| 2010/0041152 A1 | 2/2010 | Wheeler et al. |
| 2011/0244026 A1* | 10/2011 | Guild ............... A61K 31/7105 424/450 |
| 2011/0256175 A1 | 10/2011 | Hope et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1† | 9/2012 | Schrum |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0082092 A1 | 3/2016 | Hoerr et al. |
| 2016/0089424 A1 | 3/2016 | Hoerr et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhoff et al. |
| 2017/0029847 A1 | 2/2017 | Thess |
| 2017/0042814 A1 | 2/2017 | Yaworski et al. |
| 2017/0056528 A1 | 3/2017 | De Fougerolles et al. |
| 2017/0056529 A1 | 3/2017 | Thess et al. |
| 2017/0065675 A1 | 3/2017 | Bancel et al. |

(56) References Cited

U.S. PATENT DOCUMENTS

| | | | |
|---|---|---|---|
| 2017/0065727 | A1 | 3/2017 | Fotin-Mleczek et al. |
| 2017/0114378 | A1 | 4/2017 | Wochner et al. |
| 2017/0128549 | A1 | 5/2017 | Fotin-Mileczek et al. |
| 2017/0136131 | A1 | 5/2017 | Roy et al. |
| 2017/0136132 | A1 | 5/2017 | Roy et al. |
| 2017/0143631 | A1 | 5/2017 | Chen et al. |
| 2017/0143796 | A1 | 5/2017 | Schrum et al. |
| 2017/0151333 | A1 | 6/2017 | Heyes et al. |
| 2018/0161451 | A1 | 6/2018 | Fotin-Mileczek et al. |

FOREIGN PATENT DOCUMENTS

| | | |
|---|---|---|
| EP | 2449 106 | 5/2012 |
| EP | 2338 478 | 6/2013 |
| EP | 2823 809 | 1/2015 |
| WO | WO2005/026372 | 3/2005 |
| WO | WO2005/121348 A1 | 12/2005 |
| WO | 2008083949 A2 † | 7/2008 |
| WO | WO2009/127060 | 10/2009 |
| WO | WO2010042877 A1 | 4/2010 |
| WO | WO2011/068810 A1 | 6/2011 |
| WO | WO2011/141705 | 11/2011 |
| WO | WO2012/019168 | 2/2012 |
| WO | WO2012/135805 | 10/2012 |
| WO | WO2012/170930 A1 | 12/2012 |
| WO | WO2013/039857 | 3/2013 |
| WO | WO2013/039861 | 3/2013 |
| WO | WO2013/090186 A1 | 6/2013 |
| WO | WO2013/101690 | 7/2013 |
| WO | WO2013/126803 | 8/2013 |
| WO | WO2013/130161 | 9/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/158795 | 10/2014 |
| WO | WO2014/159813 | 10/2014 |
| WO | WO2015/006747 A2 | 1/2015 |
| WO | WO2015/048744 | 4/2015 |
| WO | WO2015/051169 | 4/2015 |
| WO | WO2015/051173 | 4/2015 |
| WO | WO2015/058069 | 4/2015 |
| WO | WO2015/085318 | 6/2015 |
| WO | WO2015/089511 | 6/2015 |
| WO | WO2015/011633 | 1/2016 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |
| WO | WO2017/049074 A1 | 3/2017 |
| WO | WO2017/049275 A2 | 3/2017 |
| WO | WO2017/049286 A1 | 3/2017 |

OTHER PUBLICATIONS

Felgner, P. et al., "Lipofection: A highly efficient, lipd-mediated DNA-trasnfection procedure", 1987, PNAS, vol. 84: pp. 7413-7417.*

Kober, L. et al., Biotechnol Bioeng., 2013, vol. 110, pp. 1164-1173.*

Ramezani, A. et al., Protein Exp. Purif., 2017, vol. 135: pp. 24-32.*

Su, X., et al., "In Vitro and in Vivo mRNA Delivery Using Lipid-Enveloped pH-Responsive Polymer Nanoparticles", Molecular Pharmaceutics, vol. 8, No. 3, Jun. 6, 2011 (Jun. 6, 2011), pp. 774-787.

Tavernier, G., et al, "mRNA as gene therapeutic: How to control protein expression", Journal of Controlled Release, vol. 150, No. 3, Mar. 1, 2011 (Mar. 1, 2011), pp. 238-247.

Hara et al.,"Some properties of IgG against diphtheria toxin synthesized in Xenopus oocytes containing mRNA from hybridoma", Biochimica et Biophysica Acta, 1985, vol. 85, p. 188-198.

Nakanishi et al., "New Transfection Agents Based on Liposomes ContainingBiosurfactant MEL-A", Pharmaceuticals, 5(3): 411-420 (2013).

Robinson et al., "Lipid Nanoparticle-Delivered Chemically Modified mRNA Restores Chloride Secretion in Cystic Fibrosis", Molecular Therapy 26(8): 1-13 (2018).

\* cited by examiner
† cited by third party

METHODS AND COMPOSITIONS FOR DELIVERING MRNA CODED ANTIBODIES

CROSS REFERENCE TO RELATED APPLICATIONS

This application is a national stage entry under 35 USC § 371 of International Patent Application No. PCT/US14/27717, filed Mar. 14, 2014 (the '717 application) and the present application claims the benefit of priority thereto. The present application and the '717 application each claim priority under 35 USC § 119(e) to U.S. provisional patent applications Ser. Nos. 61/784,903, filed Mar. 14, 2013, and 61/920,165, filed Dec. 23, 2013, the contents of which are hereby incorporated by reference in their entirety.

SEQUENCE LISTING

In accordance with 37 CFR 1.52(e)(5), a Sequence Listing in the form of an ASCII text file (entitled "Sequence_Listing.txt," created on Jun. 17, 2014, and 14,776 bytes in size) is incorporated herein by reference in its entirety.

BACKGROUND

Antibodies are known to have powerful therapeutic effects and are currently used for the treatment of a range of diseases including cancer, autoimmune diseases, cardiovascular disease, and transplant rejection. Traditionally, therapeutic antibodies are produced by recombinant technology, formulated and then administered to patients in need of antibody therapy. However, antibody production and formulation is highly expensive. In addition, many antibodies only have a very short half-life in vivo and therefore, may not reach their target antigen or target tissue before being degraded. To achieve desired efficacy, antibody therapy often requires high doses and frequent administration.

Gene therapy and genetic vaccination, also known as DNA vaccination, provide alternative approaches for delivery of large amounts of antibodies in vivo. However, the use of DNA as an agent in gene therapy and genetic vaccination may cause some safety concerns. For example, DNA is degraded slowly in the bloodstream. Formation of anti-DNA antibodies may occur (Gilkeson et al., J. Clin. Invest. 1995, 95: 1398-1402). The possible persistence of (foreign) DNA in the organism can thus lead to a hyperactivation of the immune system, which was known to result in splenomegaly in mice (Montheith et al., Anticancer Drug Res. 1997, 12(5): 421-432). Furthermore, DNA integration can cause mutations in the host genome by interrupting an intact gene.

SUMMARY OF THE INVENTION

The present invention provides an improved method for safer and more effective delivery of antibodies in vivo based on messenger RNA (mRNA) delivery technology. The present invention is, in part, based on the surprising discovery that production of fully assembled multi-chain antibodies can be accomplished in vivo by delivering exogenous mRNAs encoding a heavy chain and a light chain of the antibody, even when the heavy chain and light chain are delivered by separate mRNAs. As illustrated by non-limiting examples described in the Examples section below, when heavy chain and light chain encoding mRNA constructs, encapsulated in liposomes, were injected intravenously into mice, significant amounts of desired mRNA encoded antibody can be detected in mouse serum within six hours post-injection with a peak after 72 or 96 hours. The systemic expression of the antibody persisted even after three weeks post-injection. Thus, the present inventors have successfully demonstrated that multi-chain therapeutic antibodies can be delivered by mRNAs and produced by the patient's body itself, which makes it possible to eliminate the highly expensive recombinant antibody manufacturing process. In addition, contrary to the transient and vulnerable nature of mRNAs, the antibodies produced from the mRNAs are surprisingly long lasting and can achieve systemic distribution efficiently. The transient nature of mRNAs can also minimize the safety concern typically associated with foreign nucleic acids. Thus, the present invention provides a safer, cheaper and more effective antibody delivery approach for therapeutic uses.

In one aspect, the present invention provides a method of delivering an antibody in vivo, by administering to a subject in need thereof one or more mRNAs encoding a heavy chain and a light chain of an antibody, and wherein the antibody is expressed systemically in the subject. In some embodiments, the one or more mRNAs comprise a first mRNA encoding the heavy chain and a second mRNA encoding the light chain of the antibody. In some embodiments, the one or more mRNAs comprise a single mRNA encoding both the heavy chain and the light chain of the antibody.

In some embodiments, a heavy chain or light chain encoding mRNA comprises a sequence encoding a signal peptide. In some embodiments, a heavy chain or light chain encoding mRNA comprises a sequence encoding a human growth hormone (hGH) signal peptide (e.g, SEQ ID NO: 9 or SEQ ID NO: 10). In some embodiments, the sequence encoding a signal peptide sequence (e.g., SEQ ID NO:9 or SEQ ID NO:10) is linked, directly or indirectly, to the heavy chain or light chain encoding mRNA sequence at the N-terminus.

In some embodiments, the first mRNA encoding the heavy chain and the second mRNA encoding the light chain are present at a ratio ranging between approximately 10:1 to 1:10 (e.g., between approximately 9:1 to 1:9, 8:1 to 1:8, 7:1 to 1:7, 6:1 to 1:6, 5:1 to 1:5, 4:1 to 1:4, 3:1 to 1:3, or 2:1 to 1:2). In some embodiments, the first mRNA encoding the heavy chain and the second mRNA encoding the light chain are present at a ratio ranging between approximately 4:1 to 1:4. In some embodiments, the first mRNA encoding the heavy chain and the second mRNA encoding the light chain are present at a ratio of approximately 10:1, 9:1, 8:1, 7:1, 6:1, 5:1, 4:1, 3:1, 2:1 or 1:1. In some embodiments, the first mRNA encoding the heavy chain and the second mRNA encoding the light chain are present at a ratio of approximately 4:1. In some embodiments, the first mRNA encoding the heavy chain and the second mRNA encoding the light chain are present at a ratio of approximately 1:1. In some embodiments, the first mRNA encoding the heavy chain and the second mRNA encoding the light chain are present at a ratio greater than 1 (e.g., ranging between approximately 10:1 to 1:1, 9:1 to 1:1, 8:1 to 1:1, 7:1 to 1:1, 6:1 to 1:1, 5:1 to 1:1, 4:1 to 1:1, 3:1 to 1:1, or 2:1 to 1:1).

In some embodiments, the one or more mRNAs encoding the heavy chain and the light chain of the antibody are delivered via a polymer and/or lipid based delivery vehicle. In some embodiments, the one or more mRNAs encoding the heavy chain and the light chain of the antibody are encapsulated within one or more liposomes. In some embodiments, the first mRNA encoding the heavy chain and the second mRNA encoding the light chain are encapsulated in separate liposomes. In some embodiments, the first mRNA encoding the heavy chain and the second mRNA encoding the light chain are encapsulated in the same liposome. In some embodiments, the one or more liposomes comprise one or more of cationic lipid, neutral lipid, cholesterol-based lipid, and PEG-modified lipid. In some embodiments, the one or more liposomes comprise cationic lipid, neutral lipid, cholesterol-based lipid, and PEG-modified lipid.

In some embodiments, the one or more liposomes have a size no greater than about 250 nm (e.g., no greater than about 225 nm, 200 nm, 175 nm, 150 nm, 125 nm, 100 nm, 75 nm, or 50 nm). In some embodiments, the one or more liposomes have a size no greater than about 150 nm. In some embodiments, the one or more liposomes have a size no greater than about 100 nm. In some embodiments, the one or more liposomes have a size no greater than about 75 nm. In some embodiments, the one or more liposomes have a size no greater than about 50 nm.

In some embodiments, the one or more liposomes have a size ranging from about 250-10 nm (e.g., ranging from about 225-10 nm, 200-10 nm, 175-10 nm, 150-10 nm, 125-10 nm, 100-10 nm, 75-10 nm, or 50-10 nm). In some embodiments, the one or more liposomes have a size ranging from about 250-100 nm (e.g., ranging from about 225-100 nm, 200-100 nm, 175-100 nm, 150-100 nm). In some embodiments, the one or more liposomes have a size ranging from about 100-10 nm (e.g., ranging from about 90-10 nm, 80-10 nm, 70-10 nm, 60-10 nm, or 50-10 nm).

In some embodiments, the one or more mRNAs are modified to enhance stability. In some embodiments, the one or more mRNAs are modified to include a modified nucleotide, a modified sugar backbone, a cap structure, a poly A tail, a 5' and/or 3' untranslated region. In some embodiments, the one or more mRNAs are unmodified.

In some embodiments, the one or more mRNAs are administered intravenously. In some embodiments, the one or more mRNAs are administered intraperitoneally. In some embodiments, the one or more mRNAs are administered subcutaneously. In some embodiments, the one or more mRNAs are administered via pulmonary administration.

In some embodiments, the systemic expression of the antibody is detectable at least about 6 hours, 12 hours, 24 hours, 36 hours, 48 hours, 60 hours, 72 hours, 96 hours, 120 hours, 144 hours, 156 hours, 168 hours, or 180 hours post-administration (e.g., post single administration). In some embodiments, the systemic expression of the antibody is detectable at least about 1 day, 2 days, 3 days, 4 days, 5 days, 6 days, 7 days, 8 days, 9 days, 10 days, 11 days, 12 days, 13 days, 14 days, 15 days, 20 days, 22 days, 25 days, or 30 days post-administration (e.g., post single administration). In some embodiments, the systemic expression of the antibody is detectable at least about 0.5 weeks, 1 week, 1.5 weeks, 2 weeks, 2.5 weeks, 3 weeks, 3.5 weeks, 4 weeks, 4.5 weeks, 5 weeks, 5.5 weeks, 6 weeks, 6.5 weeks, 7 weeks, 7.5 weeks, or 8 weeks post-administration (e.g., post single administration). In some embodiments, the systemic expression of the antibody is detectable at least about 1 month, 2 months, 3 months, or 4 months post-administration (e.g., post single administration).

In some embodiments, the antibody is an intact immunoglobulin, (Fab)$_2$, (Fab')$_2$, Fab, Fab' or scFv. In some embodiments, the antibody is an IgG. In some embodiments, the antibody is selected from the group consisting of anti-CCL2, anti-lysyl oxidase-like-2 (LOXL2), anti-Flt-1, anti-TNF-α, anti-Interleukin-2Rα receptor (CD25), anti-TGF$_β$, anti-B-cell activating factor, anti-alpha-4 integrin, anti-BAGE, anti-β-catenin/m, anti-Bcr-abl, anti-C5, anti-CA125, anti-CAMEL, anti-CAP-1, anti-CASP-8, anti-CD4, anti-CD19, anti-CD20, anti-CD22, anti-CD25, anti-CDC27/m, anti-CD 30, anti-CD33, anti-CD52, anti-CD56, anti-CD80, anti-CDK4/m, anti-CEA, anti-CT, anti-CTL4, anti-Cyp-B, anti-DAM, anti-EGFR, anti-ErbB3, anti-ELF2M, anti-EMMPRIN, anti-EpCam, anti-ETV6-AML1, anti-HER2, anti-G250, anti-GAGE, anti-GnT-V, anti-Gp100, anti-HAGE, anti-HER-2/neu, anti-HLA-A*0201-R170I, anti-IGF-1R, anti-IL-2R, anti-IL-S, anti-MC1R, anti-myosin/m, anti-MUC1, anti-MUM-1, -2, -3, anti-proteinase-3, anti-p190 minor bcr-abl, anti-Pml/RARα, anti-PRAMS, anti-PSA, anti-PSM, anti-PSMA, anti-RAGE, anti-RANKL, anti-RU1 or RU2, anti-SAGE, anti-SART-1 or anti-SART-3, anti-survivin, anti-TEL/AML1, anti-TPI/m, anti-TRP-1, anti-TRP-2, anti-TRP-2/INT2, and anti-VEGF or anti-VEGF receptor.

In another aspect, the present invention provides a method of producing an antibody by administering to a cell a first mRNA encoding a heavy chain and a second mRNA encoding a light chain of an antibody, and wherein the antibody is produced by the cell. In some embodiments, the cell is a mammalian cell. In some embodiments, the cell is a human cell. In some embodiments, the cell is a cultured cell. In some embodiments, the cell is a cell within a living organism. In some embodiments, the antibody is expressed intracellularly. In some embodiments, the antibody is secreted by the cell.

In yet another aspect, the present invention provides compositions including a first mRNA encoding a heavy chain and a second mRNA encoding a light chain of an antibody, wherein the first mRNA and the second mRNA are encapsulated in one or more liposomes.

Among other things, the present invention also provides exemplary mRNAs encoding a heavy chain and a light chain of specific antibodies such as, for example, an anti-CCL2 antibody, and compositions containing the same. In certain embodiments, the present invention provides an mRNA encoding a heavy chain of an anti-CCL2 antibody having a sequence at least 50%, 55%, 60%, 65%, 70%, 75%, 80%, 85%, 90%, 95%, 96%, 97%, 98%, or 99% identical to SEQ ID NO:1 or SEQ ID NO:2, as described herein. In certain specific embodiments, the present invention provides an mRNA encoding a heavy chain of an anti-CCL2 antibody having a sequence of SEQ ID NO:1 or SEQ ID NO:2, as described herein. In certain embodiments, the present invention provides an mRNA encoding a light chain of an anti-CCL2 antibody having a sequence at least 50%, 55%, 60%, 65%, 70%, 75%, 80%, 85%, 90%, 95%, 96%, 97%, 98%, or 99% identical to SEQ ID NO:3 or SEQ ID NO:4, as described herein. In certain specific embodiments, the present invention provides an mRNA encoding a light chain of an anti-CCL2 antibody having a sequence of SEQ ID NO:3 or SEQ ID NO:4, as described herein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The following figures are for illustration purposes only and not for limitation.

DEFINITIONS

Figure 1:
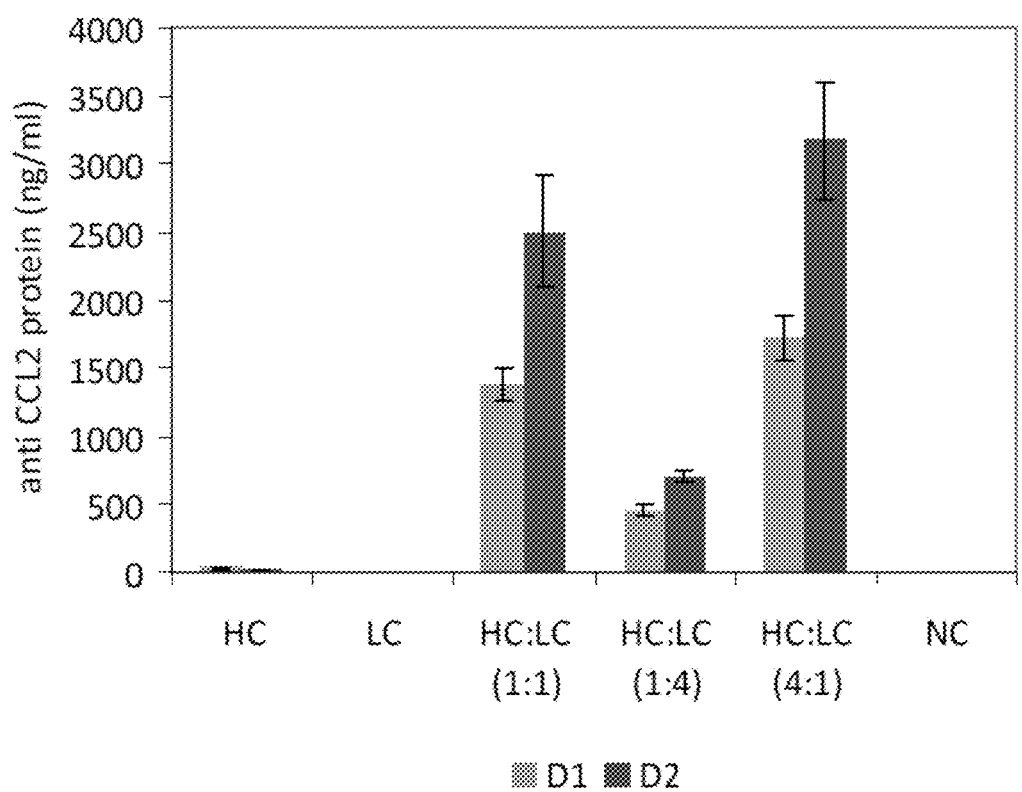
FIG. 1 shows an exemplary bar graph of IgG protein levels, as determined by ELISA, observed after treating HCL1 cells with mRNA using provided methods.

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure H$_2$N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" encompasses both intact antibody and antibody fragment. Typically, an intact "antibody" is an immunoglobulin that binds specifically to a particular antigen. An antibody may be a member of any immunoglobulin class, including any of the human classes: IgG, IgM, IgA, IgE, and IgD. A typical immunoglobulin (antibody) structural unit as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). In some embodiments, the terms "intact antibody" or "fully assembled antibody" are used in reference to an antibody to mean that it contains two heavy chains and two light chains, optionally associated by disulfide bonds as occurs with naturally-produced antibodies. In some embodiments, an antibody according to the present invention is an antibody fragment. As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Bioavailability: As used herein, the term "bioavailability" generally refers to the percentage of the administered dose that reaches the blood stream of a subject.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Expression: As used herein, "expression" of a nucleic acid sequence refers to translation of an mRNA into a polypeptide (e.g., heavy chain or light chain of antibody), assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used inter-changeably.

Functional: As used herein, a "functional" biological molecule is a biological molecule in a form in which it exhibits a property and/or activity by which it is characterized.

GC content: As used herein, the "GC content" is the fraction or percentage of total nucleobase residues in a nucleic acid sequence that are guanine residues, cytosine residues, or analogs thereof. For example, a 100 nt sequence that contains exactly 30 cytosines, exactly 30 guanines, exactly one cytosine analog, and exactly one guanine analog has a GC richness of 62%.

Half-life: As used herein, the term "half-life" is the time required for a quantity such as protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Local distribution or delivery: As used herein, the terms "local distribution," "local delivery," or grammatical equivalent, refer to tissue specific delivery or distribution. Typically, local distribution or delivery requires a protein (e.g., antibody) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for delivering antibodies in vivo based on mRNA delivery technology. In some embodiments, the present invention provides a method of delivery an antibody by administering to a subject in need of delivery one or more mRNAs encoding a heavy chain and a light chain of the antibody. In some embodiments, the heavy chain and the light chain of an antibody are delivered by separate mRNAs. In some embodiments, the heavy chain and the light chain of an antibody are delivered by a same mRNA. mRNAs may be delivered as packaged particles (e.g., encapsulated in liposomes or polymer based vehicles) or unpackaged (i.e., naked). mRNA encoded antibodies may be expressed locally (e.g., in a tissue specific manner) or systematically in the subject.

Various aspects of the invention are described in detail in the following sections. The use of sections is not meant to limit the invention. Each section can apply to any aspect of the invention. In this application, the use of "or" means "and/or" unless stated otherwise.

mRNA Coded Antibodies

The present invention may be used to deliver any type of antibodies. As used herein, the term "antibody" encompasses both intact antibody and antibody fragment. Typically, an intact "antibody" is an immunoglobulin that binds specifically to a particular antigen. An antibody may be a member of any immunoglobulin class, including any of the human classes: IgG, IgM, IgE, IgA, and IgD. Typically, an intact antibody is a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these corresponding regions on the light and heavy chain respectively. Each variable region can be further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). A light chain of immunoglobulins can be further differentiated into the isotypes kappa and lamda.

In some embodiments, the terms "intact antibody" or "fully assembled antibody" are used in reference to an antibody that contains two heavy chains and two light chains, optionally associated by disulfide bonds as occurs with naturally-produced antibodies. In some embodiments, an antibody according to the present invention is an antibody fragment.

In some embodiments, the present invention can be used to deliver an "antibody fragment." As used herein, an "antibody fragment" includes a portion of an intact antibody, such as, for example, the antigen-binding or variable region of an antibody. Examples of antibody fragments include Fab, Fab', F(ab')$_2$, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains a sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')$_2$ fragment, scFv fragment, Fv fragment, dsFv diabody, dAb fragment, Fd' fragment, Fd fragment, and an isolated complementarity determining region (CDR).

The present invention may be used to deliver any antibody known in the art and antibodies that can be produced against desired antigens using standard methods. The present invention may be used to deliver monoclonal antibodies, polyclonal antibodies, antibody mixtures or cocktails, human or humanized antibodies, chimeric antibodies, or bi-specific antibodies.

Exemplary antibodies include, but are not limited to, anti-chemokine (C—C motif) ligand 2 (CCL2), anti-lysyl oxidase-like-2 (LOXL2), anti-Flt-1, anti-TNF-α, anti-Interleukin-2Rα receptor (CD25), anti-TGF$_β$, anti-B-cell activating factor, anti-alpha-4 integrin, anti-BAGE, anti-β-catenin/m, anti-Bcr-abl, anti-C5, anti-CA125, anti-CAMEL, anti-CAP-1, anti-CASP-8, anti-CD4, anti-CD19, anti-CD20, anti-CD22, anti-CD25, anti-CDC27/m, anti-CD 30, anti-CD33, anti-CD52, anti-CD56, anti-CD80, anti-CDK4/m, anti-CEA, anti-CT, anti-CTL4, anti-Cyp-B, anti-DAM, anti-EGFR, anti-ErbB3, anti-ELF2M, anti-EMMPRIN, anti-Ep-Cam, anti-ETV6-AML1, anti-HER2, anti-G250, anti-GAGE, anti-GnT-V, anti-Gp100, anti-HAGE, anti-HER-2/neu, anti-HLA-A*0201-R170I, anti-IGF-1R, anti-IL-2R, anti-IL-5, anti-MC1R, anti-myosin/m, anti-MUC1, anti-MUM-1, -2, -3, anti-proteinase-3, anti-p190 minor bcr-abl, anti-Pml/RARα, anti-PRAMS, anti-PSA, anti-PSM, anti-PSMA, anti-RAGE, anti-RANKL, anti-RU1 or RU2, anti-SAGE, anti-SART-1 or anti-SART-3, anti-survivin, anti-TEL/AML1, anti-TPI/m, anti-TRP-1, anti-TRP-2, anti-TRP-2/INT2, and anti-VEGF or anti-VEGF receptor.

mRNAs Encoding Heavy Chain and Light Chain

According to the present invention, antibodies (e.g., intact antibodies and antibody fragments) may be produced in a cell or living organism through exogenous mRNA translation inside the cell and living organism. In particular, according to the present invention, production of fully assembled multi-chain antibodies can be accomplished in a cell or living organism by delivering exogenous mRNAs encoding a heavy chain and a light chain of the antibody. In some embodiments, a tetramer containing two heavy chains and two light chains is produced.

As used herein, the term "heavy chain" encompasses all types of naturally-occurring heavy chains of different classes of immunoglobulins, including but not limited to, IgM(μ), IgD (δ), IgG(γ), IgA(α), and IgE(ε), and biologically active variants thereof. Typically, a heavy chain according to the present invention contains the N-terminal variable region responsible for antigen recognition, typically including CDR 1, CDR 2 and CDR 3, separated by four framework regions (FR1, FR2, FR2, and FR4). Typically, the N-terminal variable region contains about 100 to 110 or more amino acids. In some embodiments, a heavy chain according to the present invention contains one or more of constant domains (e.g., $C_H1$, $C_H2$, and/or $C_H3$). In some embodiments, an mRNA encoding a heavy chain of an antibody is of or greater than 0.3 kb, 0.5 kb, 0.75 kb, 1.0 kb, 1.25 kb, 1.5 kb, 1.75 kb, 2.0 kb, 2.5 kb, 3.0 kb, 3.5 kb, 4.0 kb in length.

As used herein, the term "light chain" encompasses all types of naturally-occurring light chains of different classes of immunoglobulins, including but not limited to κ or λ isotypes, and biologically active variants thereof. Typically, a light chain according to the present invention comprises an N-terminal variable domain ($V_L$). In some embodiments, a light chain according to the present invention contains a C-terminal constant domain ($C_L$). In some embodiments, an mRNA encoding a light chain of an antibody is of or greater than 0.1 kb, 0.2 kb, 0.3 kb, 0.4 kb, 0.5 kb, 0.6 kb, 0.7 kb, 0.8 kb, 0.9 kb, 1.0 kb, 1.25 kb, 1.5 kb, 1.75 kb, 2.0 kb, 2.5 kb, or 3.0 kb in length.

Typically, a tetrameric antibody containing two heavy chains and two light chains encoded by mRNAs, each bonded together by a disulfide bridge.

According to the present invention, a heavy chain and light chain of an antibody may be encoded and delivered by a single mRNA or separate mRNAs. It is contemplated that it may be advantageous to deliver heavy chain encoding mRNA and light chain encoding mRNA at varying ratios in order to optimize production of fully assembled functional antibodies. Thus, in some embodiments, the heavy chain encoding mRNA (also referred to as the first mRNA) and the light chain encoding mRNA (also referred to as the second mRNA) are delivered at a ratio ranging between approximately 10:1 to 1:10 (e.g., between approximately 9:1 to 1:9, 8:1 to 1:8, 7:1 to 1:7, 6:1 to 1:6, 5:1 to 1:5, 4:1 to 1:4, 3:1 to 1:3, or 2:1 to 1:2). In some embodiments the heavy chain encoding mRNA (also referred to as the first mRNA) and the light chain encoding mRNA (also referred to as the second mRNA) are delivered at a ratio of or greater than approximately 10:1, 9:1, 8:1, 7:1, 6:1, 5:1, 4:1, 3:1, 2:1 or 1:1. In some embodiments, the heavy chain encoding mRNA (also referred to as the first mRNA) and the light chain encoding mRNA (also referred to as the second mRNA) are delivered at a ratio of approximately 1:1 (i.e., equal molar). In some embodiments, the heavy chain encoding mRNA (also referred to as the first mRNA) and the light chain encoding mRNA (also referred to as the second mRNA) are delivered at a ratio other than 1:1 (equal molar). For example, the heavy chain encoding mRNA (also referred to as the first mRNA) and the light chain encoding mRNA (also referred to as the second mRNA) are delivered at a ratio greater than 1 (e.g., ranging between approximately 10:1 to 1:1, 9:1 to 1:1, 8:1 to 1:1, 7:1 to 1:1, 6:1 to 1:1, 5:1 to 1:1, 4:1 to 1:1, 3:1 to 1:1, or 2:1 to 1:1). Alternatively, the heavy chain encoding mRNA (also referred to as the first mRNA) and the light chain encoding mRNA (also referred to as the second mRNA) are delivered at a ratio less than 1 (e.g., ranging between approximately 1:1 to 1:10, 1:1 to 1:9, 1:1 to 1:8, 1:1 to 1:7, 1:1 to 1:6, 1:1 to 1:5, 1:1 to 1:4, 1:1 to 1:3, or 1:1 to 1:2).

Signal Peptide

In some embodiments, an mRNA encoding a heavy chain and/or light chain incorporates a nucleotide sequence encoding a signal peptide. As used herein, the term "signal peptide" refers to a peptide present at a newly synthesized protein that can target the protein towards the secretory pathway. Typically, the signal peptide is cleaved after translocation into the endoplasmic reticulum following translation of the mRNA. Signal peptide is also referred to as signal sequence, leader sequence or leader peptide. Typically, a signal peptide is a short (e.g., 5-30, 5-25, 5-20, 5-15, or 5-10 amino acids long) peptide. A signal peptide may be present at the N-terminus of a newly synthesized protein. Without wishing to be bound by any particular theory, the incorporation of a signal peptide encoding sequence on a heavy chain and/or light chain encoding mRNA may facilitate the secretion and/or production of the antibody produced from the mRNA in vivo.

A suitable signal peptide for the present invention can be a heterogeneous sequence derived from various eukaryotic and prokaryotic proteins, in particular secreted proteins. In some embodiments, a suitable signal peptide is a leucine-rich sequence. See Yamamoto Y et al. (1989), Biochemistry, 28:2728-2732, which is incorporated herein by reference. A suitable signal peptide may be derived from a human growth hormone (hGH), serum albumin preproprotein, Ig kappa light chain precursor, Azurocidin preproprotein, cystatin-S precursor, trypsinogen 2 precursor, potassium channel blocker, alpha conotoxin lp1.3, alpha conotoxin, alfa-galactosidase, cellulose, aspartic proteinase nepenthesin-1, acid chitinase, K28 prepro-toxin, killer toxin zygocin precursor, and Cholera toxin. Exemplary signal peptide sequences are described in Kober, et al., Biotechnol. Bioeng., 110: 1164-73, 2012, which is incorporated herein by reference.

In some embodiments, a heavy chain and/or light chain encoding mRNA may incorporate a sequence encoding a signal peptide derived from human growth hormone (hGH), or a fragment thereof. A non-limiting nucleotide sequence encoding a hGH signal peptide is show below.

```
5' human growth hormone (hGH) sequence
(SEQ ID NO: 9):
AUGGCCACUGGAUCAAGAACCUCACUGCUGCUCGCUUUUGGACU

GCUUUGCCUGCCCUGGUUGCAAGAAGGAUCGGCUUUCCCGACCA

UCCCACUCUCC
```

```
Alternative 5' human growth hormone (hGH)
sequence (SEQ ID NO: 10):
AUGGCAACUGGAUCAAGAACCUCCCUCCUGCUCGCAUUCGGCCU

GCUCUGUCUCCCAUGGCUCCAAGAAGGAAGCGCGUUCCCCACUA

UCCCCCUCUCG
```

In some embodiments, an mRNA according to the present invention may incorporate a signal peptide encoding sequence having at least 50%, 55%, 60%, 65%, 70%, 75%, 80%, 85%, 90%, 95%, 96%, 97%, 98%, 99% or more identity to SEQ ID NO:9 or SEQ ID NO:10.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of antibody-coding mRNA according to the invention, a DNA template is transcribed in vitro. A suitable DNA template typically has a promoter, for example a T3, T7 or SP6 promoter, for in vitro transcription, followed by desired nucleotide sequence for desired antibody encoding (e.g., heavy chain or light chain encoding) mRNA and a termination signal.

Desired antibody encoding (e.g., heavy chain or light chain encoding) mRNA sequence according to the invention may be determined and incorporated into a DNA template using standard methods. For example, starting from a desired amino acid sequence (e.g., a desired heavy chain or light chain sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

mRNA according to the present invention may be synthesized as unmodified or modified mRNA. Typically, mRNAs are modified to enhance stability. Modifications of mRNA can include, for example, modifications of the nucleotides of the RNA. A modified mRNA according to the invention can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642, the disclosure of which is included here in its full scope by reference.

In some embodiments, antibody encoding mRNAs (e.g., heavy chain and light chain encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, antibody encoding mRNAs (e.g., heavy chain and light chain encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, antibody encoding mRNAs (e.g., heavy chain and light chain encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, antibody encoding mRNAs (e.g., heavy chain and light chain encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, antibody encoding mRNAs (e.g., heavy chain and light chain encoding mRNAs) include a 3' poly(A) tail structure. A poly-A tail on the 3' terminus of mRNA typically includes about 10 to 300 adenosine nucleotides (e.g., about 10 to 200 adenosine nucleotides, about 10 to 175 adenosine nucleotides, about 10 to 150 adenosine nucleotides, about about 10 to 125 adenosine nucleotides, 10 to 100 adenosine nucleotides, about 10 to 75 adenosine nucleotides, about 20 to 70 adenosine nucleotides, or about 20 to 60 adenosine nucleotides). In some embodiments, antibody encoding mRNAs (e.g., heavy chain and light chain encoding mRNAs) include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, antibody encoding mRNAs (e.g., heavy chain and light chain encoding mRNAs) include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length (e.g., about 50 and 400 nucleotides in length, about 50 and 300 nucleotides in length, about 50 and 200 nucleotides in length, or about 50 and 100 nucleotides in length).

In some embodiments, a 5' region of antibody encoding mRNAs (e.g., heavy chain and light chain encoding mRNAs) includes a sequence encoding a signal peptide, such as those described herein. In particular embodiments, a signal peptide derived from human growth hormone (hGH) (e.g. SEQ ID NO:9) is incorporated in the 5' region. Typically, a signal peptide encoding sequence (e.g., hGH signal peptide encoding sequence such as SEQ ID NO:9) is linked, directly or indirectly, to the heavy chain or light chain encoding sequence at the N-terminus.

Exemplary mRNAs Encoding Heavy Chain and Light Chain of Anti-CCL2

As a non-limiting example, mRNAs encoding the heavy chain and light chain of an anti-CCL2 antibody are described in Example 1. The heavy chain encoding mRNA without and with the 5' and 3' UTR sequences are shown below as SEQ ID NO:1 and SEQ ID NO:2, respectively. The light chain encoding mRNA without and with the 5' and 3' UTR sequences are shown below as SEQ ID NO:3 and SEQ ID NO:4, respectively.

```
Heavy chain anti-CCL2 (HC-αCCL2) mRNA without
5' and 3' UTR (SEQ ID NO: 1):
AUGGAAUUCGGCCUGAGCUGGCUGUUCCUGGUGGCCAUCCUGAAGGGC

GUGCAGUGCCAGGUCCAGCUGGUGCAGUCUGGCGCCGAAGUGAAGAAA

CCCGGCUCCUCCGUGAAGGUGUCCUGCAAGGCCUCCGGCGGCACCUUC

UCCAGCUACGGCAUCUCCUGGGUCCGACAGGCCCCAGGCCAGGGCCUG

GAAUGGAUGGGCGGCAUCAUCCCCAUCUUCGGCACCGCCAACUACGCC

CAGAAAUUCCAGGGCAGAGUGACCAUCACCGCCGACGAGUCCACCUCC

ACCGCCUACAUGGAACUGUCCUCCCUGCGGAGCGAGGACACCGCCGUG

UACUACUGCGCCAGAUACGACGGCAUCUACGGCGAGCUGGACUUCUGG

GGCCAGGGCACCCUGGUCACCGUGUCCUCUGCCAAGACCACCCCCCCC

UCCGUGUACCCUCUGGCCCCUGGCUCUGCCGCCCAGACCAACUCUAUG

GUCACCCUGGGCUGCCUGGUCAAGGGCUACUUCCCCGAGCCCGUGACC

GUGACCUGGAACUCCGGCUCCCUGUCCUCCGGCGUGCACACCUUCCCU

GCCGUGCUGCAGUCCGACCUCUACACCCUGUCCAGCAGCGUGACCGUG

CCCUCCUCCACCUGGCCCUCCGAGACAGUGACCUGCAACGUGGCCCAC

CCCGCCUCCAGCACCAAGGUGGACAAGAAAAUCGUGCCCCGGGACUGC

GGCUGCAAGCCCUGCAUCUGUACCGUGCCCGAGGUGUCCUCCGUGUUC

AUCUUCCCACCCAAGCCCAAGGACGUGCUGACCAUCACACUGACCCCC

AAAGUGACCUGCGUGGUGGUGGACAUCUCCAAGGACGACCCCGAGGUG

CAGUUCAGUUGGUUCGUGGACGACGUGGAAGUGCACACCGCUCAGACC

CAGCCCAGAGAGGAACAGUUCAACUCCACCUUCAGAUCCGUGUCCGAG

CUGCCCAUCAUGCACCAGGACUGGCUGAACGGCAAAGAAUUCAAGUGC

AGAGUGAACUCCGCCGCCUUCCCAGCCCCCAUCGAAAAGACCAUCUCC

AAGACCAAGGGCAGACCCAAGGCCCCCCAGGUCUACACCAUCCCCCCA

CCCAAAGAACAGAUGGCCAAGGACAAGGUGUCCCUGACCUGCAUGAUC

ACCGAUUUCUUCCCAGAGGACAUCACCGUGGAAUGGCAGUGGAACGGC

CAGCCCGCCGAGAACUACAAGAACACCCAGCCCAUCAUGGACACCGAC

GGCUCCUACUUCGUGUACUCCAAGCUGAACGUGCAGAAGUCCAACUGG

GAGGCCGGCAACACCUUCACCUGUAGCGUGCUGCACGAGGGCCUGCAC

AACCACCACACCGAGAAGUCCCUGUCCCACUCCCCCGGCAAGUGA

Heavy chain anti-CCL2 (HC-αCCL2) mRNA with 5'
and 3' UTR (SEQ ID NO: 2): (The 5' and 3' UTR
sequences are underlined)
GGACAGAUCGCCUGGAGACGCCAUCCACGCUGUUUUGACCUCCAUAGA

AGACACCGGGACCGAUCCAGCCUCCGCGGCCGGGAACGGUGCAUUGGA
```

```
ACGCGGAUUCCCCGUGCCAAGAGUGACUCACCGUCCUUGACACGAUGG

AAUUCGGCCUGAGCUGGCUGUUCCUGGUGGCCAUCCUGAAGGGCGUGC

AGUGCCAGGUCCAGCUGGUGCAGUCUGGCGCCGAAGUGAAGAAACCCG

GCUCCUCCGUGAAGGUGUCCUGCAAGGCCUCCGGCGGCACCUUCUCCA

GCUACGGCAUCUCCUGGGUCCGACAGGCCCCAGGCCAGGGCCUGGAAU

GGAUGGGCGGCAUCAUCCCCAUCUUCGGCACCGCCAACUACGCCCAGA

AAUUCCAGGGCAGAGUGACCAUCACCGCCGACGAGUCCACCUCCACCG

CCUACAUGGAACUGUCCUCCCUGCGGAGCGAGGACACCGCCGUGUACU

ACUGCGCCAGAUACGACGGCAUCUACGGCGAGCUGGACUUCUGGGGCC

AGGGCACCCUGGUCACCGUGUCCUCUGCCAAGACCACCCCCCCCUCCG

UGUACCCUCUGGCCCCUGGCUCUGCCGCCCAGACCAACUCUAUGGUCA

CCCUGGGCUGCCUGGUCAAGGGCUACUUCCCCGAGCCCGUGACCGUGA

CCUGGAACUCCGGCUCCCUGUCCUCCGGCGUGCACACCUUCCCUGCCG

UGCUGCAGUCCGACCUCUACACCCUGUCCAGCAGCGUGACCGUGCCCU

CCUCCACCUGGCCCUCCGAGACAGUGACCUGCAACGUGGCCCACCCCG

CCUCCAGCACCAAGGUGGACAAGAAAAUCGUGCCCCGGGACUGCGGCU

GCAAGCCCUGCAUCUGUACCGUGCCCGAGGUGUCCUCCGUGUUCAUCU

UCCCACCCAAGCCCAAGGACGUGCUGACCAUCACACUGACCCCCAAAG

UGACCUGCGUGGUGGUGGACAUCUCCAAGGACGACCCCGAGGUGCAGU

UCAGUUGGUUCGUGGACGACGUGGAAGUGCACACCGCUCAGACCCAGC

CCAGAGAGGAACAGUUCAACUCCACCUUCAGAUCCGUGUCCGAGCUGC

CCAUCAUGCACCAGGACUGGCUGAACGGCAAAGAAUUCAAGUGCAGAG

UGAACUCCGCCGCCUUCCCAGCCCCCAUCGAAAAGACCAUCUCCAAGA

CCAAGGGCAGACCCAAGGCCCCCCAGGUCUACACCAUCCCCCCACCCA

AGAACAGAUGGCCAAGGACAAGGUGUCCCUGACCUGCAUGAUCACCG

AUUUCUUCCCAGAGGACAUCACCGUGGAAUGGCAGUGGAACGGCCAGC

CCGCCGAGAACUACAAGAACACCCAGCCCAUCAUGGACACCGACGGCU

CCUACUUCGUGUACUCCAAGCUGAACGUGCAGAAGUCCAACUGGGAGG

CCGGCAACACCUUCACCUGUAGCGUGCUGCACGAGGGCCUGCACAACC

ACCACACCGAGAAGUCCCUGUCCCACUCCCCCGGCAAGUGACGGGUGG

CAUCCCUGUGACCCCUCCCCAGUGCCUCUCCUGGCCCUGGAAGUUGCC

ACUCCAGUGCCCACCAGCCUUGUCCUAAUAAAAUUAAGUUGCAUCAAG

CU

Light chain anti-CCL2 (LC-αCCL2) mRNA without
5' and 3' UTR (SEQ ID NO: 3):
AUGGAAACCCCUGCCCAGCUGCUGUUCCUGCUGCUGCUGUGGCUGCCU

GAUACCACCGGCGAAAUCGUGCUGACCCAGUCCCCCGCCACCCUGUCU

CUGAGCCCUGGCGAGAGAGCCACCCUGAGCUGCAGAGCCUCCCAGUCC

GUGUCCGACGCCUACCUGGCCUGGUAUCAGCAGAAGCCCGGCCAGGCC

CCUCGGCUGCUGAUCUACGACGCCUCCCUCUAGAGCCACCGGCGUGCCC

GCCAGAUUCUCCGGCUCUGGCUCUGGCACCGACUUCACCCUGACCAUC

UCCAGCCUGGAACCCGAGGACUUCGCCGUGUACUACUGCCACCAGUAC
```

-continued

AUCCAGCUGCACAGCUUCACCUUCGGCCAGGGCACCAAGGUGGAAAUC

AAGGCCGAUGCCGCCCCUACCGUGUCCAUCUUCCCACCCUCCAGCGAG

CAGCUGACCUCUGGCGGCGCUUCCGUCGUGUGCUUCCUGAACAACUUC

UACCCCAAGGACAUCAACGUGAAGUGGAAGAUCGACGGCUCCGAGCGG

CAGAACGGCGUGCUGAACUCCUGGACCGACCAGGACUCCAAGGACAGC

ACCUACUCCAUGUCCUCCACCCUGACCCUGACCAAGGACGAGUACGAG

CGGCACAACUCCUAUACCUGCGAGGCCACCCACAAGACCUCCACCUCC

CCCAUCGUGAAGUCCUUCAACCGGAACGAGUGCUGA

Light chain anti-CCL2 (LC-αCCL2) mRNA with 5'
and 3' UTR (SEQ ID NO: 4): (The 5' and 3' UTR
sequences are underlined)
<u>GGACAGAUCGCCUGGAGACGCCAUCCACGCUGUUUUGACCUCCAUAGA</u>

<u>AGACACCGGGACCGAUCCAGCCUCCGCGGCCGGGAACGGUGCAUUGGA</u>

<u>ACGCGGAUUCCCCGUGCCAAGAGUGACUCACCGUCCUUGACACGAUGG</u>

AAACCCCUGCCCAGCUGCUGUUCCUGCUGCUGCUGUGGCUGCCUGAUA

CCACCGGCGAAAUCGUGCUGACCCAGUCCCCCGCCACCCUGUCUCUGA

GCCCUGGCGAGAGAGCCACCCUGAGCUGCAGAGCCUCCCAGUCCGUGU

CCGACGCCUACCUGGCCUGGUAUCAGCAGAAGCCCGGCCAGGCCCCUC

GGCUGCUGAUCUACGACGCCUCCUCUAGAGCCACCGGCGUGCCCGCCA

GAUUCUCCGGCUCUGGCUCUGGCACCGACUUCACCCUGACCAUCUCCA

GCCUGGAACCCGAGGACUUCGCCGUGUACUACUGCCACCAGUACAUCC

AGCUGCACAGCUUCACCUUCGGCCAGGGCACCAAGGUGGAAAUCAAGG

CCGAUGCCGCCCCUACCGUGUCCAUCUUCCCACCCUCCAGCGAGCAGC

UGACCUCUGGCGGCGCUUCCGUCGUGUGCUUCCUGAACAACUUCUACC

CCAAGGACAUCAACGUGAAGUGGAAGAUCGACGGCUCCGAGCGGCAGA

ACGGCGUGCUGAACUCCUGGACCGACCAGGACUCCAAGGACAGCACCU

ACUCCAUGUCCUCCACCCUGACCCUGACCAAGGACGAGUACGAGCGGC

ACAACUCCUAUACCUGCGAGGCCACCCACAAGACCUCCACCUCCCCA

UCGUGAAGUCCUUCAACCGGAACGAGUGCUGA<u>CGGGUGGCAUCCCUGU</u>

<u>GACCCCUCCCCAGUGCCUCUCCUGGCCCUGGAAGUUGCCACUCCAGUG</u>

<u>CCCACCAGCCUUGUCCUAAUAAAAUUAAGUUGCAUCAAGCU</u>

Among other things, the present invention also provides mRNAs encoding a heavy chain and light chain of an anti-CCL2 antibody substantially identical or similar to the sequences described herein. In some embodiments, an mRNA encoding the heavy chain of an anti-CCL2 antibody has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1 or SEQ ID NO:2 as described herein. In some embodiments, an mRNA encoding the heavy chain of an anti-CCL2 antibody has a nucleotide sequence encoding an amino acid sequence at least 50%, 55%, 60%, 65%, 70%, 75%, 80%, 85%, 90%, 91%, 92%, 93%, 94%, 95%, 96%, 97%, 98%, 99% or more identical or homologous to SEQ ID NO:1 as described herein. In some embodiments, an mRNA encoding the light chain of an anti-CCL2 antibody has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3 or SEQ ID NO:4 as described herein. In some embodiments, an mRNA encoding the light chain of an anti-CCL2 antibody has a nucleotide sequence encoding an amino acid sequence at least 50%, 55%, 60%, 65%, 70%, 75%, 80%, 85%, 90%, 91%, 92%, 93%, 94%, 95%, 96%, 97%, 98%, 99% or more identical or homologous to SEQ ID NO:3 as described herein.

In some embodiments, mRNA provided herein contains one or more modified nucleotides such as those described herein. In some embodiments, an mRNA encoding the heavy chain or light chain of an anti-CCL2 antibody may contain at least 10%, at least 20%, at least 30%, at least 40%, at least 50%, at least 60%, at least 70%, at least 75%, at least 80%, at least 85%, at least 90%, or at least 95% of modified nucleotides of all modifiable nucleotides of the sequence.
Exemplary mRNAs Encoding Heavy Chain and Light Chain of Anti-VEGF Heavy chain anti-VEGF (HC-αVEGF) mRNA without 5'
and 3' UTR (SEQ ID NO: 5):
AUGGCAACUGGAUCAAGAACCUCCCUCCUGCUCGCAUUCGGCCUGCUC

UGUCUCCCAUGGCUCCAAGAAGGAAGCGCGUUCCCCACUAUCCCCCUC

UCGGAGGUUCAGCUGGUCGAAAGCGGGGGCGGCCUCGUCCAGCCAGGU

GGAUCCCUCCGCCUGAGCUGCGCCGCGUCCGGAUACACUUUCACCAAC

UACGGCAUGAACUGGGUCCGCCAGGCGCCGGGAAAGGGACUGGAAUGG

GUCGGCUGGAUCAAUACCUACACUGGAGAGCCUACCUACGCCGCUGAC

UUUAAGAGGCGGUUCACUUUCUCACUGGAUACUUCCAAGUCAACCGCU

UACCUUCAGAUGAAUUCCCUGCGCGCCGAGGAUACCGCAGUGUAUUAC

UGCGCCAAAUACCCGCAUUACUACGGCUCCAGCCACUGGUACUUUGAC

GUGUGGGGUCAAGGAACCCUGGUGACUGUGUCGUCCGCUUCCACCAAG

GGACCAAGCGUGUUCCACUCGCCCCGAGCUCAAAAUCGACGUCGGGA

GGUACUGCCGCACUGGGGUGCUUGGUCAAGGACUACUUUCCAGAGCCG

GUGACUGUUUCCUGGAACAGCGGAGCGCUCACCUCGGGCGUGCACACC

UUCCCUGCGGUGUUGCAGUCAUCUGGACUGUACUCGCUGUCCAGCGUG

GUCACGGUCCCGAGCUCGUCGCUCGGGACCCAAACCUACAUUUGCAAU

GUCAACCACAAGCCAUCGAACACCAAAGUCGACAAGAAGGUGGAACCG

AAGUCGUGCGACAAGACUCAUACGUGCCCACCGUGUCCGGCUCCGGAA

CUGUUGGGGGCCCCUCCGUGUUCCUUUUCCCGCCAAAGCCUAAGGAC

ACUCUCAUGAUCUCACGGACGCCAGAAGUGACCUGUGUGGUCGUGGAU

GUGUCACAUGAGGAUCCGGAAGUCAAAUUCAACUGGUAUGUGGACGGG

GUGGAAGUGCAUAAUGCCAAAACCAAACCUCGCGAGGAGCAGUACAAC

UCAACCUACCGGGUGGUGUCCGUGCUGACUGUGCUGCACCAGGACUGG

CUGAAUGGAAAGGAGUACAAAUGCAAGGUCAGCAACAAGGCCCUUCCC

GCCCCAAUCGAAAAGACGAUCUCGAAGGCCAAAGGUCAGCCGCGAGAG

CCUCAAGUGUACACUCUGCCGCCGUCAAGAGAAGAAAUGACUAAGAAC

CAAGUUUCCCUCACUUGCCUGGUGAAGGGCUUCUACCCCAGCGACAUC

GCAGUGGAAUGGGAGAGCAACGGACAGCCGGAAAACAACUAUAAGACC

ACCCCUCCUGUGUUGGACUCGGAUGGUUCCUUCUUCCUUUACAGCAAG

-continued
CUGACCGUGGAUAAAUCGCGGUGGCAGCAAGGAAAUGUGUUUUCAUGC
UCAGUCAUGCACGAGGCGCUGCACAAUCACUACACUCAGAAGUCCCUG
UCGCUGUCGCCAGGAAAAUAA Heavy chain anti-VEGF (HC-αVEGF) mRNA with 5' and 3' UTR (SEQ ID NO: 6): (The 5' and 3' UTR sequences are underlined, signal peptide sequences are italicized and bolded)
<u>GGACAGAUCGCCUGGAGACGCCAUCCACGCUGUUUUGACCUCCAUAGA</u>

<u>AGACACCGGGACCGAUCCAGCCUCCGCGGCCGGGAACGGUGCAUUGGA</u>

<u>ACGCGGAUUCCCCGUGCCAAGAGUGACUCACCGUCCUUGACACG</u>

*AUGGCAACUGGAUCAAGAACCUCCC*

*UCCUGCUCGCAUUCGGCCUGCUCUGUCUCCC*

*AUGGCUCCAAGAAGGAAGCGCGUUC*

*CCCACUAUCCCCCUCUCG*GAGGUUCAGCUGGUCGAAAGCGGGG
GCGGCCUCGUCCAGCCAGGUGGAUCCCUCCGCCUGAGCUGCGCCGCGU
CCGGAUACACUUUCACCAACUACGGCAUGAACUGGGUCCGCCAGGCGC
CGGGAAAGGGACUGGAAUGGGUCGGCUGGAUCAAUACCUACACUGGAG
AGCCUACCUACGCCGCUGACUUUAAGAGGCGGUUCACUUUCUCACUGG
AUACUUCCAAGUCAACCGCUUACCUUCAGAUGAAUUCCCUGCGCGCCG
AGGAUACCGCAGUGUAUUACUGCGCCAAAUACCCGCAUUACUACGGCU
CCAGCCACUGGUACUUUGACGUGUGGGGUCAAGGAACCCUGGUGACUG
UGUCGUCCGCUUCCACCAAGGGACCAAGCGUGUUUCCACUCGCCCCGA
GCUCAAAAUCGACGUCGGGAGGUACUGCCGCACUGGGGUGCUUGGUCA
AGGACUACUUUCCAGAGCCGGUGACUGUUUCCUGGAACAGCGGAGCGC
UCACCUCGGGCGUGCACACCUUCCCUGCGGUGUUGCAGUCAUCUGGAC
UGUACUCGCUGUCCAGCGUGGUCACGGUCCCGAGCUCGUCGCUCGGGA
CCCAAACCUACAUUUGCAAUGUCAACCACAAGCCAUCGAACACCAAAG
UCGACAAGAAGGUGGAACCGAAGUCGUGCGACAAGACUCAUACGUGCC
CACCGUGUCCGGCUCCGGAACUGUUGGGGGGCCCCUCCGUGUUCCUUU
UCCCGCCAAAGCCUAAGGACACUCUCAUGAUCUCACGGACGCCAGAAG
UGACCUGUGUGGUCGUGGAUGUGUCACAUGAGGAUCCGGAAGUCAAAU
UCAACUGGUAUGUGGACGGGGUGGAAGUGCAUAAUGCCAAAACCAAAC
CUCGCGAGGAGCAGUACAACUCAACCUACCGGGUGGUGUCCGUGCUGA
CUGUGCUGCACCAGGACUGGCUGAAUGGAAAGGAGUACAAAUGCAAGG
UCAGCAACAAGGCCCUUCCCGCCCCAAUCGAAAAGACGAUCUCGAAGG
CCAAAGGUCAGCCGCGAGAGCCUCAAGUGUACACUCUGCCGCCGUCAA
GAGAAGAAAUGACUAAGAACCAAGUUUCCCUCACUUGCCUGGUGAAGG
GCUUCUACCCCAGCGACAUCGCAGUGGAAUGGGAGAGCAAUGGACAGC
CGGAAAACAACUAUAAGACCACCCCUCCUGUGUUGGACUCGGAUGGUU
CCUUCUUCCUUUACAGCAAGCUGACCGUGGAUAAAUCGCGGUGGCAGC
AAGGAAAUGUGUUUUCAUGCUCAGUCAUGCACGAGGCGCUGCACAAUC
ACUACACUCAGAAGUCCCUGUCGCUGUCGCCAGGAAAAUAA<u>CGGGUGG</u>

-continued
<u>CAUCCCUGUGACCCCUCCCCAGUGCCUCUCCUGGCCCUGGAAGUUGCC</u>

<u>ACUCCAGUGCCCACCAGCCUUGUCCUAAUAAAAUUAAGUUGCAUCAAG</u>

<u>CU</u>

Light chain anti-VEGF (HC-αVEGF) mRNA without 5' and 3' UTR (SEQ ID NO: 7):
AUGGCCACUGGAUCAAGAACCUCACUGCUGCUCGCUUUUGGACUGCUU
UGCCUGCCCUGGUUGCAAGAAGGAUCGGCUUUCCCGACCAUCCCACUC
UCCGACAUUCAAAUGACGCAGUCCCCAUCGAGCCUCUCAGCAUCAGUG
GGGGAUCGCGUGACUAUCACUUGCUCGGCGAGCCAGGAUAUCAGCAAU
UACCUGAACUGGUAUCAGCAAAAGCCUGGAAAGGCACCGAAGGUGCUG
AUCUACUUCACCUCAAGCCUCCAUUCGGGUGUCCCGUCCCGCUUCAGC
GGCUCCGGCUCAGGCACUGACUUCACCCUGACUAUCUCCUCGCUGCAA
CCGGAAGAUUUCGCCACUUACUACUGUCAGCAGUACUCCACCGUGCCU
UGGACGUUCGGACAGGGAACCAAAGUUGAGAUUAAGCGGACGGUCGCG
GCCCCCUCCGUGUUUAUCUUUCCGCCUUCGGACGAGCAGCUGAAGUCG
GGAACCGCCUCUGUCGUGUGCCUCCUGAACAACUUCUACCCGCGGGAA
GCCAAGGUGCAGUGGAAAGUGGAUAACGCGCUUCAGAGCGGCAAUUCG
CAAGAGUCCGUGACCGAAGAGGACUCGAAGGACUCAACCUACUCCCUC
AGCUCAACCCUCACUUUGUCGAAGGCCGACUACGAGAAGCACAAAGUC
UACGCAUGCGAAGUCACCCACCAGGGUCUGUCGAGCCCAGUGACUAAA
UCCUUCAAUAGGGGGGAAUGUUAA Light chain anti-VEGF (HC-αVEGF) mRNA with 5' and 3' UTR (SEQ ID NO: 8): (The 5' and 3' UTR sequences are underlined, signal peptide sequences are italicized and bolded)
<u>GGACAGAUCGCCUGGAGACGCCAUCCACGCUGUUUUGACCUCCAUAGA</u>

<u>AGACACCGGGACCGAUCCAGCCUCCGCGGCCGGGAACGGUGCAUUGGA</u>

<u>ACGCGGAUUCCCCGUGCCAAGAGUGACUCACCGUCCUUGACACG</u>

*AUGGCCACUGGAUCAAGAACCUCAC*

*UGCUGCUCGCUUUUGGACUGCUUUGCCUGCC*

*CUGGUUGCAAGAAGGAUCGGCUUU*

*CCCGACCAUCCCACUCUCC*GACAUUCAAAUGACGCAGUCCCC
AUCGAGCCUCUCAGCAUCAGUGGGGGAUCGCGUGACUAUCACUUGCUC
GGCGAGCCAGGAUAUCAGCAAUUACCUGAACUGGUAUCAGCAAAAGCC
UGGAAAGGCACCGAAGGUGCUGAUCUACUUCACCUCAAGCCUCCAUUC
GGGUGUCCCGUCCCGCUUCAGCGGCUCCGGCUCAGGCACUGACUUCAC
CCUGACUAUCUCCUCGCUGCAACCGGAAGAUUUCGCCACUUACUACUG
UCAGCAGUACUCCACCGUGCCUUGGACGUUCGGACAGGGAACCAAAGU
UGAGAUUAAGCGGACGGUCGCGGCCCCCUCCGUGUUUAUCUUUCCGCC
UUCGGACGAGCAGCUGAAGUCGGGAACCGCCUCUGUCGUGUGCCUCCU
GAACAACUUCUACCCGCGGGAAGCCAAGGUGCAGUGGAAAGUGGAUAA
CGCGCUUCAGAGCGGCAAUUCGCAAGAGUCCGUGACCGAAGAGGACUC
GAAGGACUCAACCUACUCCCUCAGCUCAACCCUCACUUUGUCGAAGGC
CGACUACGAGAAGCACAAAGUCUACGCAUGCGAAGUCACCCACCAGGG

-continued

UCUGUCGAGCCCAGUGACUAAAUCCUUCAAUAGGGGGGAAUGUUAACG

GGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCA

UCAAGCU

Among other things, the present invention also provides mRNAs encoding a heavy chain and light chain of an anti-VEGF antibody substantially identical or similar to the sequences described herein. In some embodiments, an mRNA encoding the heavy chain of an anti-VEGF antibody has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:5 or SEQ ID NO:6 as described herein. In some embodiments, an mRNA encoding the heavy chain of an anti-VEGF antibody has a nucleotide sequence encoding an amino acid sequence at least 50%, 55%, 60%, 65%, 70%, 75%, 80%, 85%, 90%, 91%, 92%, 93%, 94%, 95%, 96%, 97%, 98%, 99% or more identical or homologous to SEQ ID NO:5 as described herein. In some embodiments, an mRNA encoding the light chain of an anti-VEGF antibody has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:7 or SEQ ID NO:8 as described herein. In some embodiments, an mRNA encoding the light chain of an anti-VEGF antibody has a nucleotide sequence encoding an amino acid sequence at least 50%, 55%, 60%, 65%, 70%, 75%, 80%, 85%, 90%, 91%, 92%, 93%, 94%, 95%, 96%, 97%, 98%, 99% or more identical or homologous to SEQ ID NO:7 as described herein.

In some embodiments, mRNA provided herein contains one or more modified nucleotides such as those described herein. In some embodiments, an mRNA encoding the heavy chain or light chain of an anti-VEGF antibody may contain at least 10%, at least 20%, at least 30%, at least 40%, at least 50%, at least 60%, at least 70%, at least 75%, at least 80%, at least 85%, at least 90%, or at least 95% of modified nucleotides of all modifiable nucleotides of the sequence.

As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgap-dna.CMP matrix.

Delivery Vehicles

According to the present invention, antibody encoding mRNAs (e.g., heavy chain and light chain encoding mRNAs) described herein may be delivered as naked RNA (unpackaged) or via delivery vehicles. As used herein, the terms "delivery vehicle," "transfer vehicle," or grammatical equivalent, are used interchangeably.

In some embodiments, mRNAs encoding a heavy chain and a light chain of an antibody may be delivered via a single delivery vehicle. In some embodiments, mRNAs encoding a heavy chain and a light chain of an antibody may be delivered via separate delivery vehicles. For example, mRNAs encoding a heavy chain and a light chain of an antibody may be packaged separately but delivered simultaneously. Alternatively, mRNAs encoding a heavy chain and a light chain of an antibody may be packaged separately and delivered sequentially.

According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly (D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g. a lipid nanoparticle. As used herein, liposomal delivery vehicles, e.g. lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue. The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

In some embodiments, a suitable delivery vehicle is formulated as a lipid nanoparticle. As used herein, the phrase "lipid nanoparticle" refers to a delivery vehicle comprising one or more lipids (e.g., cationic lipids, non-cationic lipids, cholesterol-based lipids, and PEG-modified lipids). The contemplated lipid nanoparticles may be prepared by including multi-component lipid mixtures of varying ratios employing one or more cationic lipids, non-cationic lipids, cholesterol-based lipids, and PEG-modified lipids. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides).

In certain embodiments of the invention, the carrier is formulated using a polymer as a carrier, alone or in combination with other carriers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

In some embodiments, a suitable delivery vehicle contains a cationic lipid. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)—N,N-dimethyl-6-(9Z,12Z)-octadeca-9,12-dien-1-yl) tetracosa-15,18-dien-1-amine (HGT5000), (15Z,18Z)—N, N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9, 12-dien-1-yl)tetracosa-5, 15, 18-trien-1-amine (HGT5002).

In some embodiments, the cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. No. 5,171,678; U.S. Pat. No. 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethyl-ammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1).

In some embodiments, one or more of the cationic lipids present in such a composition comprise at least one of an imidazole, dialkylamino, or guanidinium moiety.

In some embodiments, one or more of the cationic lipids present in such a composition are chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, one or more of the cationic lipids present in such a composition is a cationic lipid described in WO 2013063468 and in U.S. provisional application Ser. No. 61/894,299, entitled "Lipid Formulations for Delivery of Messernger RNA" filed on Oct. 22, 2013, both of which are incorporated by reference herein. In some embodiments, a cationic lipid comprises a compound of formula I-c1-a:

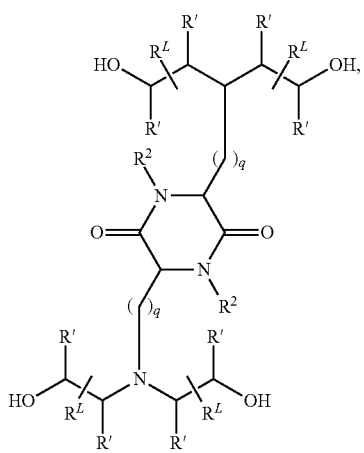

or a pharmaceutically acceptable salt thereof, wherein:

each $R^2$ independently is hydrogen or $C_{1-3}$ alkyl;

each q independently is 2 to 6;

each R' independently is hydrogen or $C_{1-3}$ alkyl;

and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

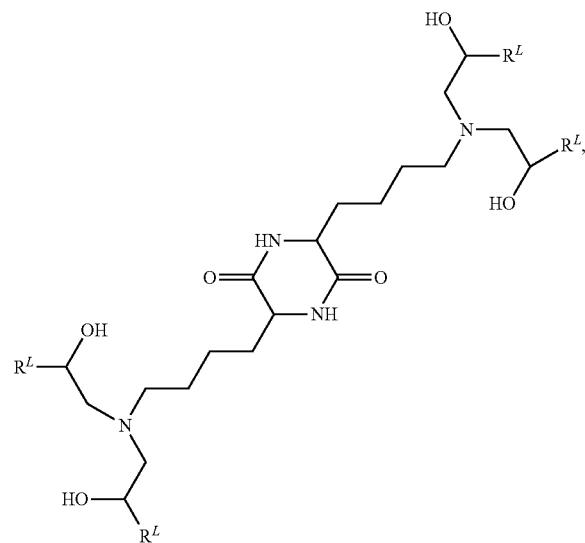

or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided compositions include a cationic lipid cKK-E12, or (3,6-bis(4-(bis(2-hydroxydodecyl)amino)butyl)piperazine-2,5-dione). Structure of cKK-E12 is shown below:

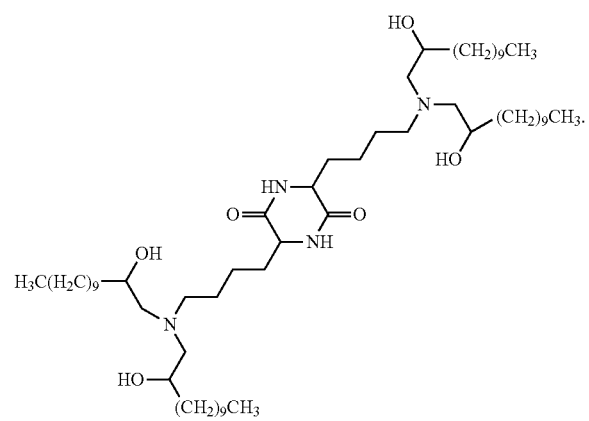

In some embodiments, a suitable delivery vehicle contains one or more non-cationic lipids, In some embodiments, a non-cationic lipid is a neutral lipid, i.e., a lipid that does not carry a net charge in the conditions under which the composition is formulated and/or administered. Such exemplary non-cationic or neutral lipids can be chosen from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), and cholesterol.

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In other embodiments, suitable lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in U.S. Provisional Application No. 61/494,745, the entire teachings of which are incorporated herein by reference in their entirety.

In addition, several reagents are commercially available to enhance transfection efficacy. Suitable examples include LIPOFECTIN (DOTMA:DOPE) (Invitrogen, Carlsbad, Calif.), LIPOFECTA INE (DOSPA:DOPE) (Invitrogen), LIPOFECTAMINE2000. (Invitrogen), FUGENE, TRANSFECTAM (DOGS), and EFFECTENE.

In some embodiments, the cationic lipid may comprise a molar ratio of about 1% to about 90%, about 2% to about 70%, about 5% to about 50%, about 10% to about 40% of the total lipid present in the transfer vehicle, or preferably about 20% to about 70% of the total lipid present in the transfer vehicle.

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle). Contemplated PEG-modified lipids include, but is not limited to, a polyethylene glycol chain of up to 5 kDa in length covalently attached to a lipid with alkyl chain(s) of C6-C20 length. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

In particular embodiments, a suitable transfer vehicle (e.g., a lipid nanoparticle) is prepared by combining multiple lipid and/or polymer components. For example, a transfer vehicle may be prepared using C12-200, DOPE, chol, DMG-PEG2K at a molar ratio of 40:30:25:5, or DODAP, DOPE, cholesterol, DMG-PEG2K at a molar ratio of 18:56:20:6, or HGT5000, DOPE, chol, DMG-PEG2K at a molar ratio of 40:20:35:5, or HGT5001, DOPE, chol, DMG-PEG2K at a molar ratio of 40:20:35:5. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly. For example, in embodiments, the percentage of cationic lipid in the lipid nanoparticle may be greater than 10%, greater than 20%, greater than 30%, greater than 40%, greater than 50%, greater than 60%, or greater than 70%. The percentage of non-cationic lipid in the lipid nanoparticle may be greater than 5%, greater than 10%, greater than 20%, greater than 30%, or greater than 40%. The percentage of cholesterol in the lipid nanoparticle may be greater than 10%, greater than 20%, greater than 30%, or greater than 40%. The percentage of PEG-modified lipid in the lipid nanoparticle may be greater than 1%, greater than 2%, greater than 5%, greater than 10%, or greater than 20%.

In certain embodiments, suitable lipid nanoparticles of the invention comprise at least one of the following cationic lipids: C12-200, DLin-KC2-DMA, DODAP, HGT4003, ICE, HGT5000, or HGT5001. In some embodiments, suitable transfer vehicle comprises cholesterol and/or a PEG-modified lipid. In some embodiments, suitable transfer vehicles comprises DMG-PEG2K. In some embodiments, suitable transfer vehicle comprises one of the following lipid combinations: C12-200, DOPE, cholesterol, DMG-PEG2K; DODAP, DOPE, cholesterol, DMG-PEG2K; HGT5000, DOPE, cholesterol, DMG-PEG2K; HGT5001, DOPE, cholesterol, DMG-PEG2K; XTC, DSPC, cholesterol, PEG-DMG; MC3, DSPC, cholesterol, PEG-DMG; and ALNY-100, DSPC, cholesterol, PEG-DSG.

The liposomal transfer vehicles for use in the compositions of the invention can be prepared by various techniques which are presently known in the art. Multilamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments of this invention, the compositions of the present invention comprise a transfer vehicle wherein the mRNA is associated on both the surface of the transfer vehicle and encapsulated within the same transfer vehicle. For example, during preparation of the compositions of the present invention, cationic liposomal transfer vehicles may associate with the mRNA through electrostatic interactions. For example, during preparation of the compositions of the present invention, cationic liposomal transfer vehicles may associate with the mRNA through electrostatic interactions.

Suitable liposomal delivery vehicles according to the present invention may be made in various sizes. Selection of an appropriate size may take into consideration the site of the target cell or tissue and to some extent the application for which the liposome is being made. In some embodiments, an appropriate size of liposomal delivery vehicles is selected to facilitate systemic distribution of antibody encoded by the mRNA. In some embodiments, it may be desirable to limit transfection of the mRNA to certain cells or tissues. For example, to target hepatocytes a liposomal transfer vehicle may be sized such that its dimensions are smaller than the fenestrations of the endothelial layer lining hepatic sinusoids in the liver; accordingly the liposomal transfer vehicle can readily penetrate such endothelial fenestrations to reach the target hepatocytes. Alternatively, a liposomal transfer vehicle may be sized such that the dimensions of the liposome are of a sufficient diameter to limit or expressly avoid distribution into certain cells or tissues. For example, a liposomal transfer vehicle may be sized such that its dimensions are larger than the fenestrations of the endothelial layer lining hepatic sinusoids to thereby limit distribution of the liposomal transfer vehicle to hepatocytes.

In some embodiments, a suitable liposomal delivery vehicle has a size no greater than about 250 nm (e.g., no greater than about 225 nm, 200 nm, 175 nm, 150 nm, 125 nm, 100 nm, 75 nm, or 50 nm). In some embodiments, a suitable liposomal delivery vehicle has a size ranging from about 250-10 nm (e.g., ranging from about 225-10 nm, 200-10 nm, 175-10 nm, 150-10 nm, 125-10 nm, 100-10 nm, 75-10 nm, or 50-10 nm). In some embodiments, a suitable liposomal delivery vehicle has a size ranging from about 250-100 nm (e.g., ranging from about 225-100 nm, 200-100 nm, 175-100 nm, 150-100 nm). In some embodiments, a suitable liposomal delivery vehicle has a size ranging from about 100-10 nm (e.g., ranging from about 90-10 nm, 80-10 nm, 70-10 nm, 60-10 nm, or 50-10 nm).

A variety of alternative methods known in the art are available for sizing of a population of liposomal transfer vehicles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Expression of RNA Coded Antibodies In Vivo

According to the present invention, antibody encoding mRNAs (e.g., heavy chain and light chain encoding mRNAs) described herein may be delivered, with or without delivery vehicles, to a subject in need of delivery such that a fully assembled desired antibody is expressed in vivo.

In some embodiments, a desired antibody encoded by mRNAs is expressed systemically in the subject. This can be achieved by secreting fully assembled antibodies from a cell or tissue in which the antibody is initially expressed into the circulation system of the subject. For example, compositions of the invention containing antibody encoding mRNAs and lipososmal vehicles distribute into the cells of the liver to facilitate the delivery and the subsequent expression of the mRNA comprised therein by the cells of the liver (e.g., hepatocytes). The targeted hepatocytes may function as a biological "reservoir" or "depot" capable of producing, and excreting a fully assembled desired antibody, resulting in systemic distribution of the antibody. In other embodiments, cells other than hepatocytes (e.g., lung, spleen, heart, ocular, or cells of the central nervous system) can serve as a depot location for protein production. Typically, sustained production and secretion of fully assembled antibodies from the reservoir or depot cells results in effective systemic distribution.

In some embodiments, systemic expression of a desired antibody encoded mRNAs in the patient serum (i.e., blood) is detectable for more than 1 hour, more than 4 hours, more than 6 hours, more than 12 hours, more than 18 hours, more than 24 hours, more than 30 hours, more than 36 hours, more than 42 hours, more than 48 hours, more than 54 hours, more than 60 hours, more than 66 hours, more than 72 hours, more than 96 hours, more than 120 hours, more than 144 hours, more than 168 hours, more than 2 weeks, more than 3 weeks, more than 1 month or more than 2 months after administration. In some embodiments, the serum concentration of the antibody encoded by mRNAs reaches a peak level about 6 hours, 12 hours, 18 hours, 24 hours, 30 hours, 36 hours, 42 hours, 48 hours, 54 hours, 60 hours, 66 hours, 72 hours, 78 hours, 84 hours, 90 hours, or 96 hours after administration. In some embodiments, sustained circulation of the desired antibody encoded by mRNAs are observed. For example, the systemic expression of the antibody encoded by mRNAs in the patient serum (i.e., blood) may be detected for more than 1 day, 2 days, 3 days, 4 days, 5 days, 1 week, 2 weeks, 3 weeks, 1 month, 2 months or more after administration.

In some embodiments, mRNAs encoding heavy chain and light chain of an antibody may be delivered to target cells or tissues for intracellular expression or local distribution of the antibody. Typically, local distribution results when a fully assembled antibody is produced and secreted from a target cell to the surrounding extracellular fluid without entering the circulation system, such as blood stream. As used herein, the term "target cell" or "target tissue" refers to a cell or tissue to which antibody encoding mRNA(s) is to be directed or targeted. For example, where it is desired to deliver an mRNA to a hepatocyte, the hepatocyte represents the target cell. Antibody encoding mRNAs (e.g., heavy chain and light chain encoding mRNAs) described herein may be delivered to a variety of target cells or tissues including, but not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Delivery of mRNAs to target cells and tissues may be accomplished by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide means to passively direct the delivery of the compositions to such target cells.

Alternatively, delivery of mRNAs to target cells and tissues may be accomplished by active targeting, which involves the use of additional excipients, referred to herein as "targeting ligands" that may be bound (either covalently or non-covalently) to the transfer vehicle to encourage localization of such transfer vehicle at certain target cells or target tissues. For example, targeting may be mediated by the inclusion of one or more endogenous targeting ligands (e.g., apolipoprotein E) in or on the transfer vehicle to encourage distribution to the target cells or tissues. Recognition of the targeting ligand by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a ligand capable of enhancing affinity of the composition to the target cell. Targeting ligands may be linked to the outer bilayer of the lipid particle during formulation or post-formulation. These methods are well known in the art. In addition, some lipid particle formulations may employ fusogenic polymers such as PEAA, Hemagglutinin, other lipopeptides (see U.S. patent application Ser. Nos. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more ligands (e.g., peptides, aptamers, oligonucleotides, a vitamin or other molecules) that are capable of enhancing the affinity of the compositions and their nucleic acid contents for the target cells or tissues. Suitable ligands may optionally be bound or linked to the surface of the transfer vehicle. In some embodiments, the targeting ligand may span the surface of a transfer vehicle or be encapsulated within the transfer vehicle. Suitable ligands and are selected based upon their physical, chemical or biological properties (e.g., selective affinity and/or recognition of target cell surface markers or features) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor or mannose receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the transfer vehicle (e.g., a lipid nanoparticle) therefore facilitate recognition and uptake of the compositions of the present invention in target cells and tissues. Examples of suitable targeting ligands include one or more peptides, proteins, aptamers, vitamins and oligonucleotides.

As used herein, the term "subject" refers to any animal (e.g., a mammal), including, but not limited to, humans, non-human primates, rodents, and the like, to which the mRNAs and compositions of the present invention are administered. Typically, the terms "subject" and "patient" are used interchangeably herein in reference to a human subject.

Pharmaceutical Composition and Administration

To facilitate expression of antibodies in vivo, antibody encoding mRNAs (e.g., heavy chain and light chain encoding mRNAs) and delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Antibody encoding mRNAs and compositions containing the same may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient antibody production.

Suitable routes of administration include, for example, oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections.

Alternately, mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present invention complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In one embodiment, the compositions of the invention are formulated such that they are suitable for extended-release of the mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomal vehicles which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

Also contemplated herein are lyophilized pharmaceutical compositions comprising one or more of the liposomal nanoparticles disclosed herein and related methods for the use of such lyophilized compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Expression of RNA Coded Antibodies In Vitro

In some embodiments, antibody encoding mRNAs (e.g., heavy chain and light chain encoding mRNAs) may be used to produce antibodies in vitro. For example, cells may be transfected by antibody encoding mRNAs (e.g., heavy chain and light chain encoding mRNAs) and cultured under cell culture conditions that allow the production of the antibody by the cells. In some embodiments, the antibody is expressed intracellularly. In other embodiments, the antibody is secreted by the cells such that the antibody may be harvested from the supernatant.

In some embodiments, mammalian cells are used in accordance with the present invention. Non-limiting examples of mammalian cells include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Standard cell culture media and conditions may be used to cultivate transfected cells and produce desired antibodies encoded by mRNAs.

EXAMPLES

Example 1. Production of mRNA

Heavy chain anti-chemokine (C—C motif) ligand 2 (HC-αCCL2, SEQ ID NO: 1) and light chain anti-CCL2 (LC-αCCL2, SEQ ID NO: 2) were synthesized by in vitro transcription from a plasmid DNA template encoding the gene, which was followed by the addition of a 5' cap structure (Cap1) according to known methods (see Fechter, P.; Brownlee, G. G. "Recognition of mRNA cap structures by viral and cellular proteins" *J. Gen. Virology* 2005, 86, 1239-1249) and a 3' poly(A) tail of approximately 200 nucleotides in length as determined by gel electrophoresis. The sequences for HC-αCCL2 and LC-αCCL2 were as shown below, and 5' and 3' untranslated regions present in each mRNA product are represented as X and Y, respectively, and defined below:

```
Heavy chain anti-CCL2 (HC-αCCL2) mRNA:
X₁AUGGAAUUCGGCCUGAGCUGGCUGUUCCUGGUGGCCAUCCUGAAGG

GCGUGCAGUGCCAGGUCCAGCUGGUGCAGUCUGGCGCCGAAGUGAAGA

AACCCGGCUCCUCCGUGAAGGUGUCCUGCAAGGCCUCCGGCGGCACCU

UCUCCAGCUACGGCAUCUCCUGGGUCCGACAGGCCCCAGGCCAGGGCC

UGGAAUGGAUGGGCGGCAUCAUCCCCAUCUUCGGCACCGCCAACUACG

CCCAGAAAUUCCAGGGCAGAGUGACCAUCACCGCCGACGAGUCCACCU

CCACCGCCUACAUGGAACUGUCCUCCCUGCGGAGCGAGGACACCGCCG

UGUACUACUGCGCCAGAUACGACGGCAUCUACGGCGAGCUGGACUUCU

GGGGCCAGGGCACCCUGGUCACCGUGUCCUCUGCCAAGACCACCCCCC

CCUCCGUGUACCCUCUGGCCCCUGGCUCUGCCGCCCAGACCAACUCUA

UGGUCACCCUGGGCUGCCUGGUCAAGGGCUACUUCCCCGAGCCCGUGA

CCGUGACCUGGAACUCCGGCUCCCUGUCCUCCGGCGUGCACACCUUCC

CUGCCGUGCUGCAGUCCGACCUCUACACCCUGUCCAGCAGCGUGACCG

UGCCCUCCUCCACCUGGCCCUCCGAGACAGUGACCUGCAACGUGGCCC

ACCCCGCCUCCAGCACCAAGGUGGACAAGAAAAUCGUGCCCCGGGACU
```

-continued

GCGGCUGCAAGCCCUGCAUCUGUACCGUGCCCGAGGUGUCCUCCGUGU

UCAUCUUCCCACCCAAGCCCAAGGACGUGCUGACCAUCACACUGACCC

CCAAAGUGACCUGCGUGGUGGUGGACAUCUCCAAGGACGACCCCGAGG

UGCAGUUCAGUUGGUUCGUGGACGACGUGGAAGUGCACACCGCUCAGA

CCCAGCCCAGAGAGGAACAGUUCAACUCCACCUUCAGAUCCGUGUCCG

AGCUGCCCAUCAUGCACCAGGACUGGCUGAACGGCAAAGAAUUCAAGU

GCAGAGUGAACUCCGCCGCCUUCCCAGCCCCCAUCGAAAAGACCAUCU

CCAAGACCAAGGGCAGACCCAAGGCCCCCCAGGUCUACACCAUCCCCC

CACCCAAAGAACAGAUGGCCAAGGACAAGGUGUCCCUGACCUGCAUGA

UCACCGAUUUCUUCCCAGAGGACAUCACCGUGGAAUGGCAGUGGAACG

GCCAGCCCGCCGAGAACUACAAGAACACCCAGCCCAUCAUGGACACCG

ACGGCUCCUACUUCGUGUACUCCAAGCUGAACGUGCAGAAGUCCAACU

GGGAGGCCGGCAACACCUUCACCUGUAGCGUGCUGCACGAGGGCCUGC

ACAACCACCACACCGAGAAGUCCCUGUCCCACUCCCCCGGCAAGUGA$Y_1$

Light chain anti-CCL2 (LC-αCCL2) mRNA:
$X_1$AUGGAAACCCUGCCCAGCUGCUGUUCCUGCUGCUGCUGUGGCUGC

CUGAUACCACCGGCGAAAUCGUGCUGACCCAGUCCCCCGCCACCCUGU

CUCUGAGCCCUGGCGAGAGAGCCACCCUGAGCUGCAGAGCCUCCCAGU

CCGUGUCCGACGCCUACCUGGCCUGGUAUCAGCAGAAGCCCGGCCAGG

CCCCUCGGCUGCUGAUCUACGACGCCUCCUCUAGAGCCACCGGCGUGC

CCGCCAGAUUCUCCGGCUCUGGCUCUGGCACCGACUUCACCCUGACCA

UCUCCAGCCUGGAACCCGAGGACUUCGCCGUGUACUACUGCCACCAGU

ACAUCCAGCUGCACAGCUUCACCUUCGGCCAGGGCACCAAGGUGGAAA

UCAAGGCCGAUGCCGCCCCUACCGUGUCCAUCUUCCCACCCUCCAGCG

AGCAGCUGACCUCUGGCGGCGCUUCCGUCGUGUGCUUCCUGAACAACU

UCUACCCCAAGGACAUCAACGUGAAGUGGAAGAUCGACGGCUCCGAGC

GGCAGAACGGCGUGCUGAACUCCUGGACCGACCAGGACUCCAAGGACA

GCACCUACUCCAUGUCCUCCACCCUGACCCUGACCAAGGACGAGUACG

AGCGGCACAACUCCUAUACCUGCGAGGCCACCCACAAGACCUCCACCU

CCCCCAUCGUGAAGUCCUUCAACCGGAACGAGUGCUGA$Y_1$

5' and 3' UTR Sequences:
$X_1$ =
GGACAGAUCGCCUGGAGACGCCAUCCACGCUGUUUUGACCUCCAUAGA

AGACACCGGGACCGAUCCAGCCUCCGCGGCCGGGAACGGUGCAUUGGA

ACGCGGAUUCCCCGUGCCAAGAGUGACUCACCGUCCUUGACACG $Y_1$ =
CGGGUGGCAUCCCUGUGACCCCUCCCCAGUGCCUCUCCUGGCCCUGGA

AGUUGCCACUCCAGUGCCCACCAGCCUUGUCCUAAUAAAAUUAAGUUG

CAUCAAGCU

Example 2. In Vitro mRNA Transfection Materials and Conditions

A. Exemplary Lipid Materials

The lipid formulations used for transfection in the examples herein consisted of one or more lipids or a multi-component lipid mixture of varying ratios employing one or more cationic lipids, helper lipids and PEGylated lipids designed to encapsulate various nucleic acid-based materials. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (see Heyes, J.; Palmer, L.; Bremner, K.; MacLachlan, I. "Cationic lipid saturation influences intracellular delivery of encapsulated nucleic acids" *J. Contr. Rel.* 2005, 107, 276-287), DLin-KC2-DMA (see Semple, S. C. et al. "Rational Design of Cationic Lipids for siRNA Delivery" *Nature Biotech.* 2010, 28, 172-176), C12-200 (Love, K. T. et al. "Lipid-like materials for low-dose in vivo gene silencing" *PNAS* 2010, 107, 1864-1869), HGT4003, ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

B. Experimental Formulations

In these experiments, aliquots of 50 mg/mL ethanolic solutions of C12-200, DOPE, cholesterol and DMG-PEG2K were mixed and diluted with ethanol to 3 mL final volume. Separately, an aqueous buffered solution (10 mM citrate/150 mM NaCl, pH 4.5) of HC-αCCL2 mRNA and LC-αCCL2 mRNA (1:1 wt:wt) mRNA was prepared by addition of 500 microgram of each construct from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.35 mg/mL αCCL2 mRNA (encapsulated). $Z_{ave}$=89.2 nm ($Dv_{(50)}$=64.0 nm; $Dv_{(90)}$=115 nm).

Example 3. Detection of Antibody after In Vitro mRNA Transfection

A. Via ELISA

In this example, F96 MaxiSorp Nunc-Immuno Plates were coated with 100 µl of 1 µg/ml of goat anti mouse IgG1 (Invitrogen A10538) in sodium carbonate buffer, pH 9.6 and incubated 1 hr at 37° C. After washing 3× with wash buffer (1×PBS, 0.05% Tween 20), the wells were blocked with 320 µl blocking buffer (1×PBS, 0.05% Tween 20, 2% BSA) for 1 hr at 37° C. Serial dilutions of monoclonal IgG standards were prepared in blocking buffer in the range from 250-0 ng/ml. Serial dilutions of the samples were prepared in blocking buffer to be in the range of the standard curve (1:100 to 1:10,000). Both samples and standards were incubated 1 hr at 37° C. After washing 3× with wash buffer, goat anti mouse IgG Fc HRP conjugated secondary antibody (Pierce 31439) was used at 1:40,000 dilution and incubated at 37° C. for 1 hr. After washing 3× with wash buffer TMB EIA substrate reagent was prepared according to manufactures instructions. After 15 min incubation at 37° C., the reaction was stopped by adding 2N $H_2SO_4$ and the plate read at 450 nm.

B. Via Western Blot

In this example, conditioned medium from transfected 293T cells or electroporated HCL2 cells were fractionated by SDS-PAGE and transferred to a polyvinylidene difluoride membrane using a transfer apparatus according to the manufacturer's instructions (Invitrogen). After incubation with 5% non-fat dry milk in TBST (10 mM Tris, pH 8.0, 150 mM NaCl, 0.5% Tween 20) for 1 hr, the membrane was washed three times with PBST and incubated with goat anti mouse IgG1 (Invitrogen A10538) for 1 hr at RT. Membranes were washed three times in PBST and incubated with 1:5000 dilution of horseradish peroxidase conjugated anti-mouse secondary antibody (Promega W4021) for 1 hr at RT. Blots were washed in PBST three more times and developed with the ECL system (Amersham Bioscience) according to manufacturer's instructions.

Example 4. In Vitro Analysis of αCCL2 Antibody Produced from Transfection of HC-αCCL2 and LC-αCCL2

Both HC-αCCL2 and LC-αCCL2 mRNA were produced as described above in Example 1. Subsequently, in accordance with Example 2A and B, HC-αCCL2 and LC-αCCL2 mRNA was transfected into either HCL1 (i.e., human cell line 1) cells or HCL2 cells in various rations (wt:wt) according to known methods.

Figure 2:
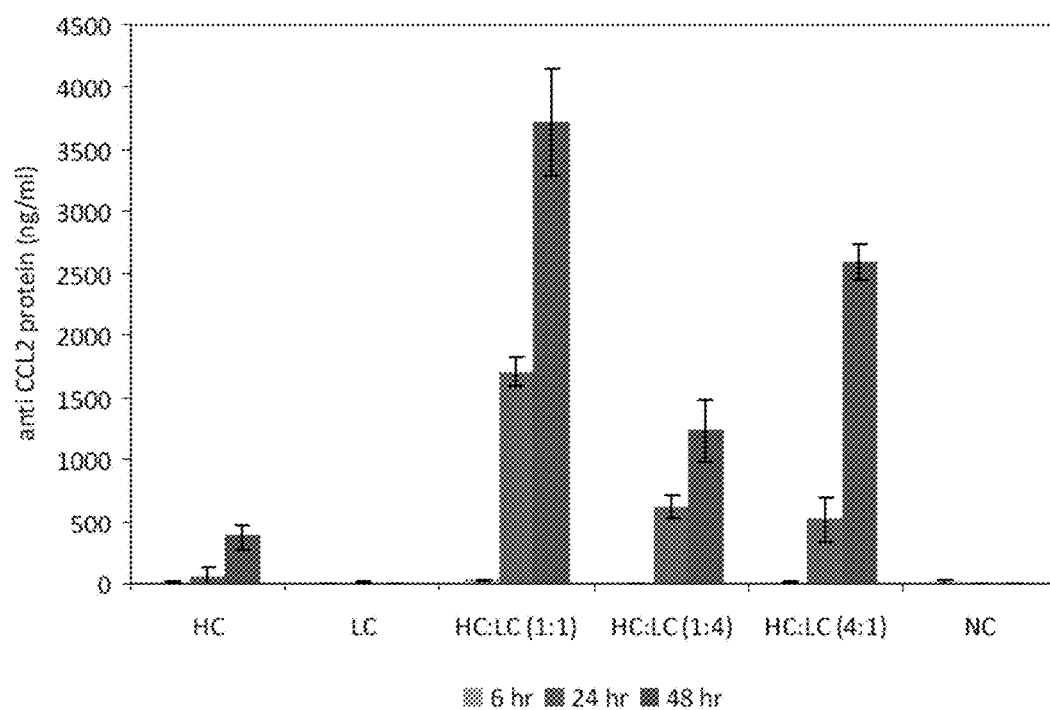
FIG. 2 shows an exemplary bar graph of IgG protein levels, as determined by ELISA, observed after treating cells with mRNA using provided methods.

The results of these studies in HCL1 cells and HCL2 cells are demonstrated in FIGS. 1 and 2, respectively. Various mixtures of α-CCL2 (chemokine (C—C motif) ligand 2) heavy chain and light chain mRNA constructs were mixed (wt:wt) and transfected into either HCL1 cells (FIG. 1) or HCL2 cells (FIG. 2). Cell supernatants were harvested at select time points post-transfection and analyzed for the presence of anti-mouse IgG using ELISA-based methods as described above in Example 3A.

As shown in FIGS. 1 and 2, varying the ratio of heavy chain to light chain (wt:wt) produced a significant difference in protein production as determined via ELISA. While a 1:1 (wt:wt) mixture of heavy chain:light chain α-CCL2 mRNA provided strong signal in HCL2 cells, a 4:1 (wt:wt) ratio provided higher protein production in HCL1 cells. While there were differences among the varying ratios, strong protein production was observed for all ratios tested. Further, in both cases, 48 hr post-transfection (Day 2, or D2) gave the strongest signal of desired protein in this example.

Figure 3:
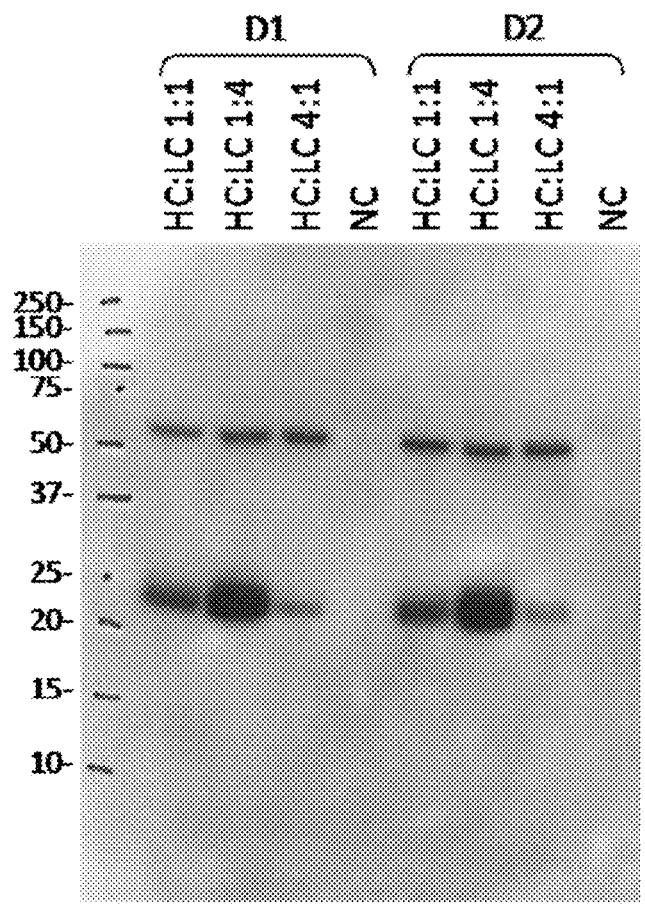
FIG. 3 depicts the results of a western blot examining protein levels resulting from introduction of mRNA, according to provided methods, in HCL1 cells after 24 and 48 hours.

To further confirm the presence of the exogenous mRNA-derived antibody, immunoblot (Western) techniques were employed for additional characterization (see FIG. 3) of HCL1-derived samples. Heavy chain and light chain fragments were successfully detected in the supernatant of mRNA transfected HCL1 cells using western blot methods as described in example 3B. Samples were analyzed 24 and 48 hours post-transfection of various mixtures of α-CCL2 heavy chain and light chain mRNA constructs (wt:wt). Band intensities observed were reflective of the mRNA ratios employed in each example.

Example 5. In Vivo Analysis of αCCL2 Antibody Produced from Intravenously Administered mRNA-Loaded Nanoparticles In this example, production of fully processed antibody was accomplished in vivo via delivery of exogenous messenger RNA, specifically, α-CCL2 heavy chain and light chain mRNA constructs (HC-αCCL2:LC-αCCL2 mRNA, 1:1 (wt:wt)) were encapsulated in cationic lipid nanoparticles as described in Example 2A and delivered to mice as a single bolus, intravenous injection.

Briefly, male CD-1 mice of approximately 6-8 weeks of age at the beginning of each experiment were used. Samples of encapsulated HC-αCCL2 mRNA and LC-αCCL2 mRNA (1:1 wt:wt) were introduced by a single bolus tail-vein injection of an equivalent total dose of 30 micrograms. Mice were sacrificed and perfused with saline at the designated time points.

The liver and spleen of each mouse was harvested, apportioned into three parts, and stored in either 10% neutral buffered formalin or snap-frozen and stored at −80° C. for analysis.

All animals were euthanized by $CO_2$ asphyxiation at given time points post dose administration followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum was extracted. For interim blood collections, approximately 40-50 μL of whole blood was collected via facial vein puncture or tail snip. Samples collected from non-treatment animals were used as baseline levels for comparison to study animals.

For ELISA analysis of αCCL2 antibody production, F96 MaxiSorp Nunc-Immuno Plate were coated with 100 ml of 1 mg/ml of MCP-1 recombinant rabbit purified monoclonal antibody in carbonate buffer, pH 9.6 and incubated 1 hr at 37° C. After washing 3× with wash buffer (1×PBS, 0.05% Tween 20), the wells were blocked with 320 ml blocking buffer (1×PBS, 0.05% Tween 20, 2% BSA) for 1 hr at 37° C. Approximately 100 ng/ml MCP-1 human or mouse recombinant protein was added to each well and incubated for 1 hr at 37° C. After washing 3× with wash buffer, serial dilutions of the samples (1:5 to 1:200) were added and incubated for 1 hr at 37° C. After washing 3× with wash buffer, goat anti-mouse IgG Fc HRP conjugated secondary antibody was used at 1:40,000 dilution and incubated at 37° C. for 1 hr. After washing 3× with wash buffer TMB EIA substrate reagent was prepared according to manufactures instructions. After 15 min incubation at 37° C., the reaction was stopped by adding 2N $H_2SO_4$ and the plate read at 450 nm.

Figure 4:
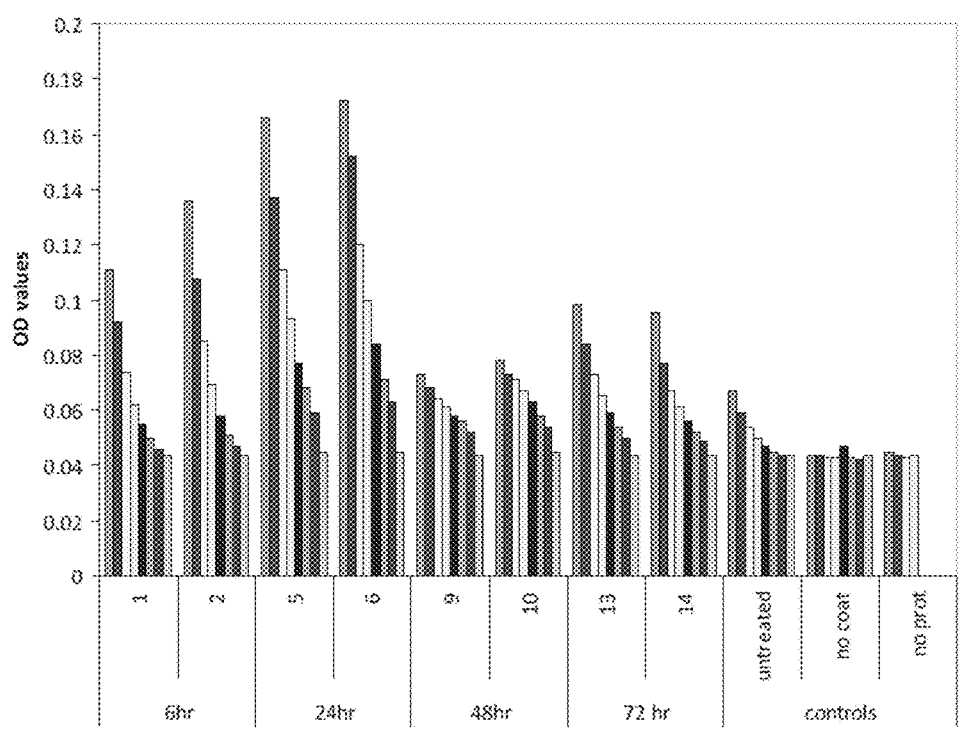
FIG. 4 shows an exemplary bar graph of CCL2 antibody levels as determined via ELISA in the serum of mice exposed to mRNA according to provided methods for 6, 24, 48, or 72 hours.

Serum levels of treated mice were monitored at select time points post-administration (6 hr, 24 hr, 48 hr, 72 hr). The levels of fully formed α-human CCL2 antibody present in mouse serum were quantified using ELISA-based methods (see FIG. 4). A significant increase in the desired, exogenous α-CCL2 mRNA derived antibody can be observed within six hours post-administration with a peak after 24 hours.

Example 6. In Vivo α-VEGF Antibody Production

In this example, production of fully processed α-VEGF antibody was accomplished in vivo via delivery of exogenous messenger RNA.

The sequences for HC-αVEGF and LC-αVEGF are as shown below, and 5' and 3' untranslated regions present in each mRNA product are represented as X and Y, respectively, and defined below:

Heavy chain anti-VEGF (HC-αVEGF) mRNA:
<u>X$_1$</u>AUGGCAACUGGAUCAAGAACCUCCCUCCUGCUCGCAUUCGGCCUGC
UCUGUCUCCCAUGGCUCCAAGAAGGAAGCGCGUUCCCCACUAUCCCCC
UCUCGGAGGUUCAGCUGGUCGAAAGCGGGGGCGGCCUCGUCCAGCCAG

GUGGAUCCCUCCGCCUGAGCUGCGCCGCGUCCGGAUACACUUUCACCA

ACUACGGCAUGAACUGGGUCCGCCAGGCGCCGGGAAAGGGACUGGAAU

GGGUCGGCUGGAUCAAUACCUACACUGGAGAGCCUACCUACGCCGCUG

ACUUUAAGAGGCGGUUCACUUUCUCACUGGAUACUUCCAAGUCAACCG

CUUACCUUCAGAUGAAUUCCCUGCGCGCCGAGGAUACCGCAGUGUAUU

ACUGCGCCAAAUACCCGCAUUACUACGGCUCCAGCCACUGGUACUUUG

ACGUGUGGGGUCAAGGAACCCUGGUGACUGUGUCGUCCGCUUCCACCA

AGGGACCAAGCGUGUUUCCACUCGCCCCGAGCUCAAAAUCGACGUCGG

GAGGUACUGCCGCACUGGGGUGCUUGGUCAAGGACUACUUUCCAGAGC

CGGUGACUGUUUCCUGGAACAGCGGAGCGCUCACCUCGGGCGUGCACA

CCUUCCCUGCGGUGUUGCAGUCAUCUGGACUGUACUCGCUGUCCAGCG

UGGUCACGGUCCCGAGCUCGUCGCUCGGGACCCAAACCUACAUUUGCA

AUGUCAACCACAAGCCAUCGAACACCAAAGUCGACAAGAAGGUGGAAC

CGAAGUCGUGCGACAAGACUCAUACGUGCCCACCGUGUCCGGCUCCGG
AACUGUUGGGGGGCCCCUCCGUGUUCCUUUUCCCGCCAAAGCCUAAGG
ACACUCUCAUGAUCUCACGGACGCCAGAAGUGACCUGUGUGGUCGUGG

AUGUGUCACAUGAGGAUCCGGAAGUCAAAUUCAACUGGUAUGUGGACG

GGGUGGAAGUGCAUAAUGCCAAAACCAAACCUCGCGAGGAGCAGUACA

ACUCAACCUACCGGGUGGUGUCCGUGCUGACUGUGCUGCACCAGGACU

GGCUGAAUGGAAAGGAGUACAAAUGCAAGGUCAGCAACAAGGCCCUUC

CCGCCCCAAUCGAAAAGACGAUCUCGAAGGCCAAAGGUCAGCCGCGAG

AGCCUCAAGUGUACACUCUGCCGCCGUCAAGAGAAGAAAUGACUAAGA
ACCAAGUUUCCCUCACUUGCCUGGUGAAGGGCUUCUACCCCAGCGACA
UCGCAGUGGAAUGGGAGAGCAACGGACAGCCGGAAAACAACUAUAAGA

CCACCCCUCCUGUGUUGGACUCGGAUGGUUCCUUCUUCCUUUACAGCA

AGCUGACCGUGGAUAAAUCGCGGUGGCAGCAAGGAAAUGUGUUUUCAU

GCUCAGUCAUGCACGAGGCGCUGCACAAUCACUACACUCAGAAGUCCC
UGUCGCUGUCGCCAGGAAAAUAA<u>Y$_1$</u>

Light chain anti-VEGF (LC-αVEGF) mRNA:
<u>X$_1$</u>AUGGCCACUGGAUCAAGAACCUCACUGCUGCUCGCUUUUGGACUGC
UUUGCCUGCCCUGGUUGCAAGAAGGAUCGGCUUUCCCGACCAUCCCAC

UCUCCGACAUUCAAAUGACGCAGUCCCCAUCGAGCCUCUCAGCAUCAG

UGGGGGAUCGCGUGACUAUCACUUGCUCGGCGAGCCAGGAUAUCAGCA

AUUACCUGAACUGGUAUCAGCAAAAGCCUGGAAAGGCACCGAAGGUGC
UGAUCUACUUCACCUCAAGCCUCCAUUCGGGUGUCCCGUCCCGCUUCA
GCGGCUCCGGCUCAGGCACUGACUUCACCCUGACUAUCUCCUCGCUGC

AACCGGAAGAUUUCGCCACUUACUACUGUCAGCAGUACUCCACCGUGC
CUUGGACGUUCGGACAGGGAACCAAAGUUGAGAUUAAGCGGACGGUCG -continued CGGCCCCCUCCGUGUUUAUCUUUCCGCCUUCGGACGAGCAGCUGAAGU
CGGGAACCGCCUCUGUCGUGUGCCUCCUGAACAACUUCUACCCGCGGG

AAGCCAAGGUGCAGUGGAAAGUGGAUAACGCGCUUCAGAGCGGCAAUU

CGCAAGAGUCCGUGACCGAAGAGGACUCGAAGGACUCAACCUACUCCC

UCAGCUCAACCCUCACUUUGUCGAAGGCCGACUACGAGAAGCACAAAG

UCUACGCAUGCGAAGUCACCCACCAGGGUCUGUCGAGCCCAGUGACUA
AAUCCUUCAAUAGGGGGGAAUGUUAA<u>Y$_1$</u>

5' and 3' UTR Sequences:
$X_1$ (5' UTR Sequence) =
GGACAGAUCGCCUGGAGACGCCAUCCACGCUGUUUUGACCUCCAUAGA

AGACACCGGGACCGAUCCAGCCUCCGCGGCCGGGAACGGUGCAUUGGA
ACGCGGAUUCCCCGUGCCAAGAGUGACUCACCGUCCUUGACACG $Y_1$ (3' UTR Sequence) =
CGGGUGGCAUCCCUGUGACCCCUCCCCAGUGCCUCUCCUGGCCCUGGA

AGUUGCCACUCCAGUGCCCACCAGCCUUGUCCUAAUAAAAUUAAGUUG

Figure 5:
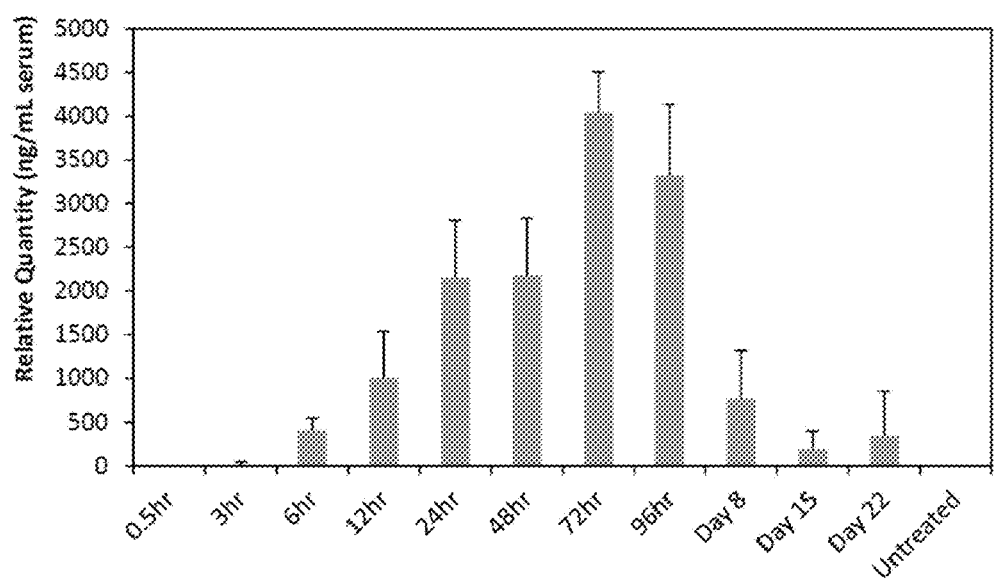
FIG. 5 shows an exemplary bar graph of α-VEGF antibody levels as determined via ELISA in the serum of mice after single dose of α-VEGF mRNA.
Figure 6:
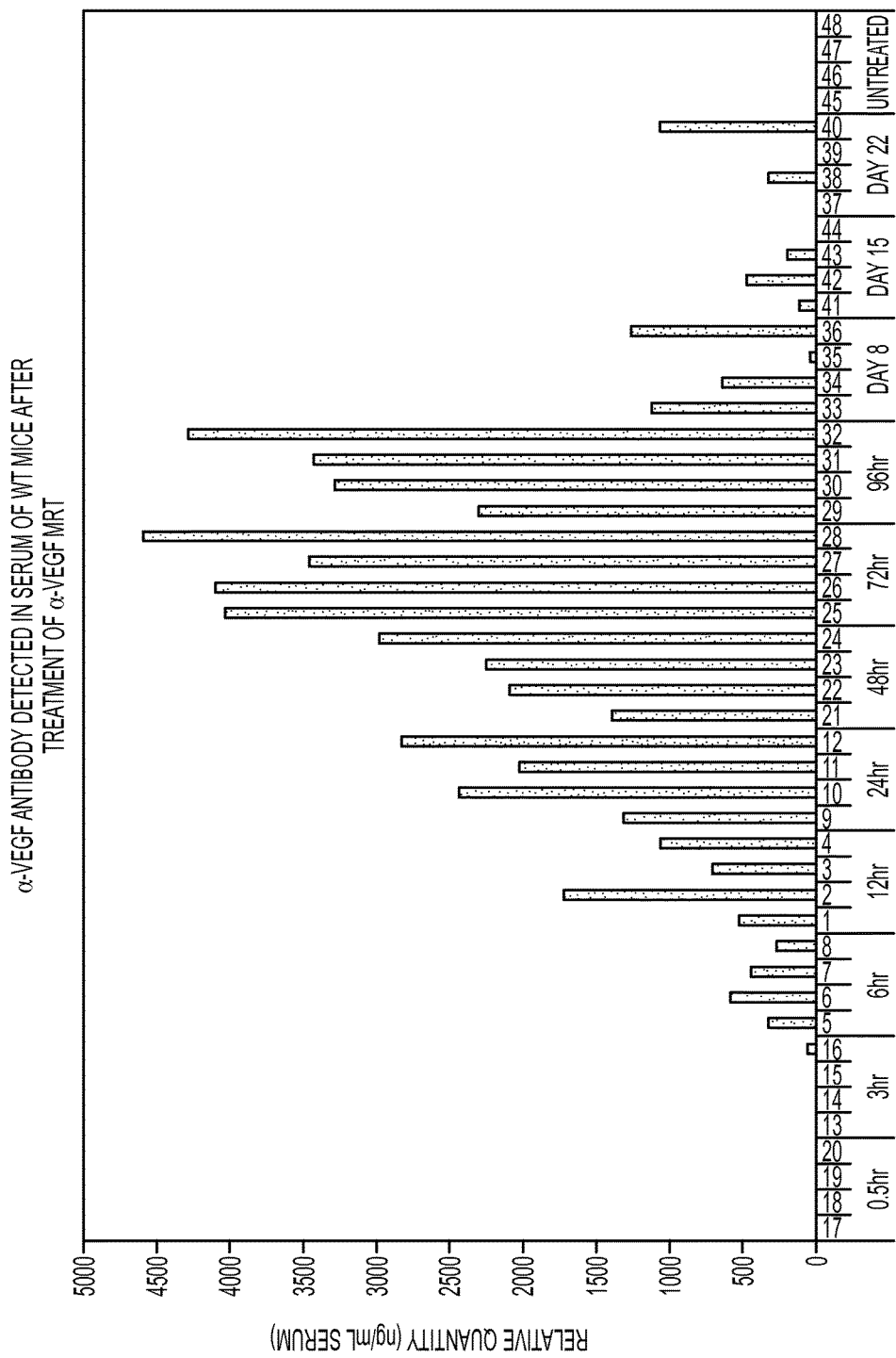
FIG. 6 shows an exemplary bar graph of α-VEGF antibody levels as determined via ELISA in the serum of individually identified mice after single dose of α-VEGF mRNA.
Figure 7:
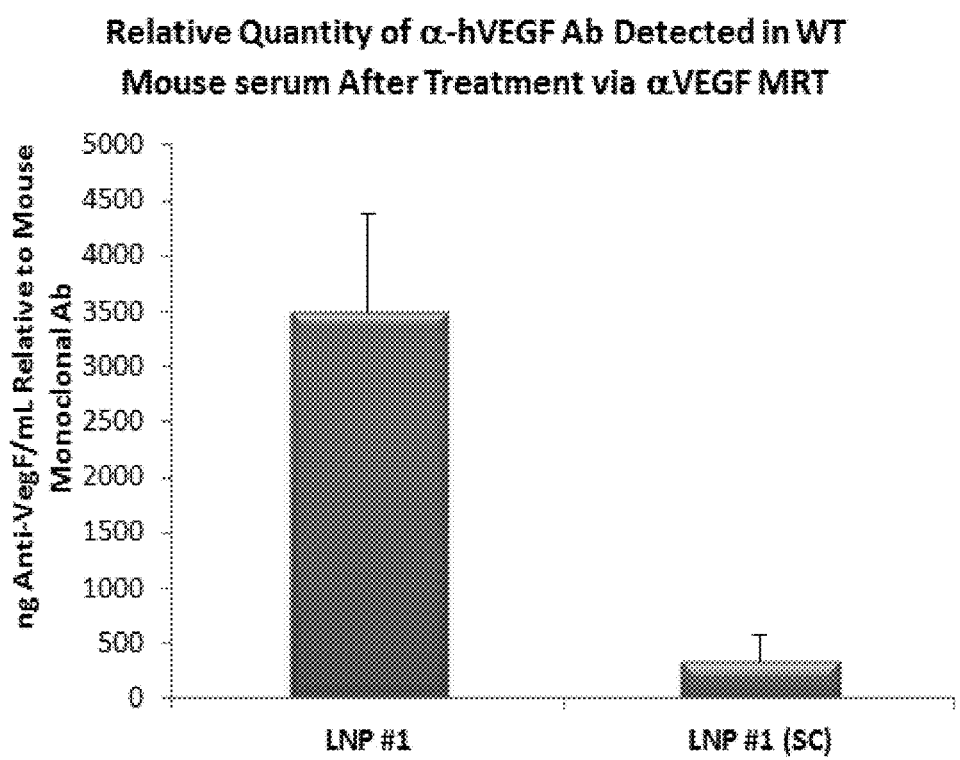
FIG. 7 shows an exemplary bar graph of in vivo production of an anti-human VEGF antibody in wild type mice 24 hours after dosing with α-VEGF mRNA loaded cKK-E12 lipid nanoparticles (LNP). Mice were dosed via either tail vein injection or subcutaneous (SC) injection.

CAUCAAGCU α-VEGF heavy chain and light chain mRNA constructs (HC-α-VEGF:LC-α-VEGF mRNA, 1:1 (wt:wt)) were encapsulated in cationic lipid nanoparticles as described below:

In these experiments, aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of HC-αCVEGF mRNA and LC-αVEGF mRNA (1:1 wt:wt) mRNA was prepared by addition of 500 microgram of each construct from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL αVEGF mRNA (encapsulated). $Z_{ave}$=81.0 nm (PDI=0.16).

HC-α-VEGF and LC-α-VEGF mRNA loaded lipid nanoparticles were delivered to wild type mice either by a single intravenous tail vein injection or subcutaneous injection at a dosage of 1.0 mg/kg and the production of anti-VEGF antibody was monitored over time in serum via ELISA.

Briefly, male CD-1 mice of approximately 6-8 weeks of age at the beginning of each experiment were used. Samples of encapsulated HC-α-VEGF mRNA and LC-α-VEGF mRNA (1:1 wt:wt) were introduced by a single bolus tail-vein injection of an equivalent total dose of 1.0 mg/kg (~30 micrograms). Mice were sacrificed and perfused with saline at the designated time points (0.50 hour, 3 hours, six hours, 12 hours, 24 hours, 48 hours, 72 hours, 96 hours, 1 week, 2 weeks, 3 weeks post-administration.

All animals were euthanized by $CO_2$ asphyxiation at given time points post dose administration followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum was extracted. For interim blood collections, approximately 40-50 µL of whole blood was collected via facial vein puncture or tail snip. Samples collected from non-treatment animals were used as baseline levels for comparison to study animals For ELISA analysis of α-VEGF antibody production, F96 MaxiSorp Nunc-Immuno Plate were coated with 100 microliters of 0.50 microgram/mL/well of recombinant human VEGF protein (Invitrogen #PHC9391) in coating buffer (50 mM NaHCO$_3$, pH9.6). After washing 3× with wash buffer, wells were blocked using a blocking buffer (1×DPBS, 2% BSA, 0.05% Tween-20) for one hour at 37° C. Upon further washing as described above, mouse serum collected from injected mice were added to each well and rabbit anti-human IgG Fc HRP (Pierce #PA-28587) conjugated secondary antibody was used at 1:10,000 dilution and incubated at 37° C. for 1 hr. After washing 3× with wash buffer TMB EIA substrate reagent was prepared according to manufactures instructions. After 10 min incubation at 37° C., the reaction was stopped by adding 2N H$_2$SO$_4$ and the plate read at 450 nm. Serum levels of treated mice were monitored at select time points post-administration (e.g., 0.5 hr, 3 hr, 6 hr, 12 hr, 24 hr, 48 hr, 72 hr, 96 hr, 8 days and 15 days). FIG. 5 depicts exemplary results illustrating α-VEGF antibody detected in serum of wild type mice after single dose of HC-α-VEGF mRNA and LC-α-VEGF mRNA loaded nanoparticles. A significant increase in the desired, exogenous α-VEGF mRNA derived antibody can be observed within six hours post-administration with a peak after 24 hours and continued out to 2 weeks after a single dose of α-VEGF mRNA. FIG. 6 depicts the same exemplary results as FIG. 5, but plotted by specific mouse number. FIG. 7 shows a comparison of the levels of α-VEGF antibody present in the serum of mice injected either intravenously or subcutaneously after 24 hours.

This example provides further confirmation that mRNA based therapy can be used for effective in vivo antibody production.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of delivering an antibody in vivo, the method comprising:
    administering systemically to a subject in need thereof a first mRNA polynucleotide encoding a heavy chain and a second mRNA polynucleotide encoding a light chain of the antibody,
    wherein the first mRNA polynucleotide and the second mRNA polynucleotide are separate, each comprising SEQ ID NO: 9 encoding a signal peptide sequence;
    wherein the first mRNA and the second mRNA are encapsulated in liposomes, each liposome comprising a cationic lipid, a non-cationic lipid and a PEG-modified lipid; and
    wherein the antibody is detectable in the serum of the subject for more than 72 hours post-administration.

2. The method of claim 1, wherein the first mRNA polynucleotide and the second mRNA polynucleotide are present at a ratio ranging between approximately 10:1 to 1:10.

3. The method of claim 2, wherein the first mRNA polynucleotide and the second mRNA polynucleotide are present at a ratio of approximately 4:1.

4. The method of claim 2, wherein the first mRNA polynucleotide-and the second mRNA polynucleotide are present at a ratio of approximately 1:1.

5. The method of claim 1, wherein the each liposome comprises cationic lipids, neutral lipids, cholesterol-based lipids, and PEG-modified lipids.

6. The method of claim 1, wherein the liposomes have an average size no greater than about 150 nm, 100 nm, or 75 nm.

7. The method of claim 1, wherein the first and second mRNA polynucleotides are modified to include a modified nucleotide.

8. The method of claim 1, wherein the first and second mRNA polynucleotides are unmodified.

9. The method of claim 1, wherein the first and second mRNAs are administered intravenously or intraperitoneally.

10. The method of claim 1, wherein the antibody is detectable in the serum of the subject at least about, 96 hours or 120 hours post-administration.

11. The method of claim 1, wherein the antibody is an intact immunoglobulin.

12. The method of claim 1, wherein the first mRNA and the second mRNA polynucleotides are encapsulated in a same liposome.

13. The method of claim 1, wherein the first mRNA and the second mRNA polynucleotides are encapsulated in separate liposomes.

14. The method of claim 1, wherein the cationic lipids constitute 5% to 50% of the total lipids in the liposome.

15. The method of claim 1, wherein the cationic lipids constitute 10% to 40% of the total lipids in the liposome.

16. The method of claim 1, wherein the PEG-modified lipids constitute 0.5% to 20% of the total lipids in the liposome.

17. The method of claim 1, wherein the PEG-modified lipids constitute 4% to 10% of the total lipids in the liposome.

* * * * *

SEQUENCE LISTING

<160> NUMBER OF SEQ ID NOS: 10

<210> SEQ ID NO 1
<211> LENGTH: 1389
<212> TYPE: RNA
<213> ORGANISM: Artificial Sequence
<220> FEATURE:
<223> OTHER INFORMATION: chemically synthesized oligonucleotide

<400> SEQUENCE: 1

```
auggaauucg gccugagcug gcuguuccug guggccaucc ugaagggcgu gcagugccag      60
guccagcugg ugcagucugg cgccgaagug aagaaacccg gcuccuccgu gaaggugucc     120
ugcaaggccu ccggcggcac cuucuccagc uacggcaucu ccgggguccg acaggcccca     180
ggccagggcc uggaauggau gggcggcauc auccccaucu ucggcaccgc caacuacgcc     240
cagaaauucc agggcagagu gaccaucacc gccgacgagu ccaccuccac cgccuacaug     300
gaacugaccu cccugcggag cgaggacacc gccguguacu acugcgccag auacgacggc     360
aucuacggcg agcuggacuu cuggggccag ggcacccugg ucaccguguc cucugccaag     420 accaccccccc ccuccgugua ccccucuggcc ccuggcucug ccgcccagac caacucuaug     480
gucacccugg gcugccuggu caagggcuac uuccccgagc ccgugaccgu gaccuggaac     540
uccggcuccc uguccuccgg cgugcacacc uucccugccg ugcugcaguc cgaccucuac     600
acccugucca gcagcgugac cgugcccucc uccaccuggc ccuccgagac agugaccugc     660
aacguggccc accccgccuc cagcaccaag guggacaaga aaaucgugcc ccgggacugc     720
ggcugcaagc ccugcaucug uaccgugccc gagguguccu ccguguucau cuucccaccc     780
aagcccaagg acgugcugac caucacacug acccccaaag ugaccugcgu gguggaccau     840
aucuccaagg acgaccccga ggugcaguuc aguugguucg uggacgacgu ggaagugcac     900
accgcucaga cccagcccag agaggaacag uucaacucca ccuucagauc cguguccgag     960
cugcccauca ugcaccagga cuggcugaac ggcaaagaau ucaagugcag agugaacucc    1020
gccgccuucc cagcccccau cgaaaagacc aucuccaaga ccaagggcag acccaaggcc    1080
ccccaggucu acaccaucco cccacccaaa gaacagaugg ccaaggacaa gguguccug    1140 accugcauga ucaccgauuu cuucccagag gacauccacg uggaauggca guggaacggc    1200
```

| cagcccgccg agaacuacaa gaacacccag cccaucaugg acaccgacgg cuccuacuuc | 1260 |
| guguacucca agcugaacgu gcagaagucc aacugggagg ccggcaacac cuucaccugu | 1320 |
| agcgugcugc acgagggccu gcacaaccac cacaccgaga aguccccuguc ccacuccccc | 1380 |
| ggcaaguga | 1389 |

<210> SEQ ID NO 2
<211> LENGTH: 1634
<212> TYPE: RNA
<213> ORGANISM: Artificial Sequence
<220> FEATURE:
<223> OTHER INFORMATION: chemically synthesized oligonucleotide

<400> SEQUENCE: 2

| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg auggaauucg ccugagcug gcuguuccug gugccaucc | 180 |
| ugaagggcgu gcagugccag guccagcugg ugcagucugg cgccgaagug aagaaacccg | 240 |
| gcucccccgu gaaggugucc ugcaaggccu ccggcggcac cuucuccagc uacggcaucu | 300 |
| ccugggucccg acaggcccca ggccagggcc uggaauggau gggcggcauc aucccccaucu | 360 |
| ucggcaccgc caacuacgcc cagaaauucc agggcagagu gaccaucacc gccgacgagu | 420 |
| ccaccuccac cgccuacaug aacugguccu cccugcggag cgaggacacc gccguguacu | 480 |
| acugcgccag auacgacggc aucuacgcg agcuggacuu cuggggccag ggcacccugg | 540 |
| ucaccguguc cucugccaag accacccccc cuccgugua cccucuggcc ccuggcucug | 600 |
| ccgcccagac caacucuaug ucacccugg gcugccuggu caagggcuac uuccccgagc | 660 |
| ccgugaccgu gaccuggaac uccggcuccc uguccuccgg cgugcacacc uucccugccg | 720 |
| ugcucgcaguc cgaccucuac acccugucca gcagcgugac cgugccccuc uccaccggc | 780 |
| ccuccgagac agugaccugc aacguggccc accccgccuc cagcaccaag guggacaaga | 840 |
| aaaucgugcc ccgggacugc ggcugcaagc ccugcaucug uaccgugccc gaggugccu | 900 |
| ccguguucau cuucccaccc aagcccaagg acgugcugac caucacacug accccccaaag | 960 |
| ugaccugcgu gguggggac aucuccaagg acgaccccga ggugcaguuc aguuguucg | 1020 |
| uggacgacgu ggaagugcac accgcucaga cccagcccag agaggaacag uucaacucca | 1080 |
| ccuucagauc cguguccgag cugcccauca ugcaccagga cuggcugaac ggcaaagaau | 1140 |
| ucaagugcag agugaacucc gccgccuucc cagccccau cgaaaagacc aucuccaaga | 1200 |
| ccaagggcag acccaaggcc cccaggucu acaccaucc cccacccaaa gaacagaugg | 1260 |
| ccaaggacaa gguccccug accugcauga ucaccgauuu cuccccagag acaucaccg | 1320 |
| uggaauggca guggaacggc cagcccgccg agaacuacaa gaacacccag cccaucaugg | 1380 |
| acaccgacgg cuccuacuuc guguacucca agcugaacgu gcagaagucc aacugggagg | 1440 |
| ccggcaacac cuucaccugu agcgugcugc acgagggccu gcacaaccac cacaccgaga | 1500 |
| aguccccuguc ccacuccccc ggcaagugac gggguggcauc ccugugaccc cuccccagug | 1560 |
| ccucuccugg cccuggaagu ugccacucca gugcccacca gccuugccu aauaaaauua | 1620 |
| aguugcauca agcu | 1634 |

<210> SEQ ID NO 3
<211> LENGTH: 708
<212> TYPE: RNA

<213> ORGANISM: Artificial Sequence
<220> FEATURE:
<223> OTHER INFORMATION: chemically synthesized oligonucleotide

<400> SEQUENCE: 3

```
auggaaaccc cugcccagcu gcuguuccug cugcugcugu ggcugccuga uaccaccggc      60
gaaaucgugc ugacccaguc ccccgccacc cugucucuga gcccuggcga gagagccacc     120
cugagcugca gagccuccca guccgugucc gacgccuacc uggccuggua ucagcagaag     180
cccggccagg ccccucggcu gcugaucuac gacgccuccu cuagagccac cggcgugccc     240
gccagauucu ccggcucugg ucucuggcacc gacuucaccc ugaccaucuc cagccuggaa    300
cccgaggacu ucgccgugua cuacugccac caguacaucc agcugcacag cuucaccuuc     360
ggccagggca ccaaggugga aaucaaggcc gaugccgccc uaccgugucc caucuuccca    420
cccuccagcg agcagcugac cucuggcggc gcuuccgucg ugugcuuccu gaacaacuuc    480
uaccccaagg acaucaacgu gaaguggaag aucgacggcu ccgagcggca aacggcgug     540
cugaacuccu ggaccgacca ggacuccaag gacagcaccu acuccaugu cuccacccug     600
acccugacca aggacgagua cgagcggcac aacuccuaua ccugcgaggc cacccacaag    660
accuccaccu cccccaucgu gaaguccuuc aaccggaacg agugcuga                 708
```

<210> SEQ ID NO 4
<211> LENGTH: 953
<212> TYPE: RNA
<213> ORGANISM: Artificial Sequence
<220> FEATURE:
<223> OTHER INFORMATION: chemically synthesized oligonucleotide

<400> SEQUENCE: 4

```
ggacagaucg ccuggagacg ccauccacgc uguuugacc uccauagaag acaccgggac       60
cgauccagcc uccgcggccg ggaacggugc auuggaacgc ggauuccccg ugccaagagu     120
gacucaccgu ccuugacacg auggaaaccc cugcccagcu gcuguuccug cugcugcugu     180
ggcugccuga uaccaccggc gaaaucgugc ugacccaguc ccccgccacc cugucucuga     240
gcccuggcga gagagccacc cugagcugca gagccuccca guccgugucc gacgccuacc    300
uggccuggua ucagcagaag cccggccagg ccccucggcu gcugaucuac gacgccuccu    360
cuagagccac cggcgugccc gccagauucu ccggcucugg ucucuggcacc gacuucaccc   420
ugaccaucuc cagccuggaa cccgaggacu ucgccgugua cuacugccac caguacaucc    480
agcugcacag cuucaccuuc ggccagggca ccaaggugga aaucaaggcc gaugccgccc    540
uaccgugucc caucuuccca cccuccagcg agcagcugac cucuggcggc gcuuccgucg    600
ugugcuuccu gaacaacuuc uaccccaagg acaucaacgu gaaguggaag aucgacggcu    660
ccgagcggca aacggcgug cugaacuccu ggaccgacca ggacuccaag gacagcaccu    720
acuccaugu cuccacccug acccugacca aggacgagua cgagcggcac aacuccuaua    780
ccugcgaggc cacccacaag accuccaccu cccccaucgu gaaguccuuc aaccggaacg    840
agugcugacg gguggcaucc cugugacccc uccccagugc cucuccuggc ccuggaaguu    900
gccacuccag ugcccaccag ccuuguccua auaaaauuaa guugcaucaa gcu           953
```

<210> SEQ ID NO 5
<211> LENGTH: 1461
<212> TYPE: RNA
<213> ORGANISM: Artificial Sequence
<220> FEATURE:
<223> OTHER INFORMATION: chemically synthesized oligonucleotide

<400> SEQUENCE: 5

```
auggcaacug gaucaagaac cucccuccug cucgcauucg gccugcucug ucucccaugg      60
cuccaagaag gaagcgcguu ccccacuauc ccccucucgg agguucagcu ggucgaaagc     120
ggggcggcc ucguccagcc agguggaucc uccgccuga gcugcgccgc guccggauac       180
acuuucacca acuacggcau gaacuggguc cgccaggcgc cgggaaaggg acuggaaugg    240
gucggcugga ucaauaccua cacuggagag ccuaccuacg ccgcugacuu uaagaggcgg    300
uucacuuucu cacuggauac uuccaaguca accgcuuacc uucagaugaa uucccugcgc    360
gccgaggaua ccgcagugua uuacugcgcc aaauacccgc auuacuacgg uccagccac     420
ugguacuuug acguggggg ucaaggaacc cuggugacug ugucguccgc uuccaccaag     480
ggaccaagcg uguuccacu cgccccgagc ucaaaaucga cgucgggagg uacugccgca    540
cuggggugcu uggucaagga cuacuuucca gagccgguga cuguuccug aacagcgga     600
gcgcucaccu cgggcgugca caccuucccu gcggguguuc agucaucugg acuguacucg   660
cuguccagcg uggucacggu cccgagcucg ucgcucggga cccaaaccua cauuugcaau   720
gucaaccaca agccaucgaa caccaaaguc gacaagaagg uggaaccgaa gucgugcgac  780
aagacucaua cgugcccacc gugucccggcu ccggaacugu uggggggccc cuccguguuc  840
cuuuucccgc caaagccuaa ggacacucuc augaucucac ggacgccaga agugaccugu  900
guggucgugg augugucaca ugaggauccg gaagucaaau caacgguua ugguggacggg  960
guggaagugc auaaugccaa aaccaaaccu cgcgaggagc aguacaacuc aaccuaccgg 1020
gugguguccg ugcugacugu gcugcaccag gacuggcuga auggaaagga guacaaaugc 1080
aaggucagca acaaggcccu uccgccccca aucgaaaaga cgaucucgaa ggccaaaggu 1140
cagccgcgag agcucaagu guacacucug ccgccgucaa gagaagaaau gacuaagaac 1200
caaguuccc ucacuugccu ggugaagggc uucuacccca gcgacaucgc aguggaaugg 1260
gagagcaacg gacagccgga aaacaacuau aagaccaccc cuccuguguu ggacucggau 1320
gguuccuucu uccuuuacag caagcugacc guggauaaau cgcgguggca gcaaggaaau 1380
guguuuucau gcucagucau gcacgaggcg cugcacaauc acuacacuca gaagucccug 1440
ucgcugucgc caggaaaaua a                                            1461
```

<210> SEQ ID NO 6
<211> LENGTH: 1706
<212> TYPE: RNA
<213> ORGANISM: Artificial Sequence
<220> FEATURE:
<223> OTHER INFORMATION: chemically synthesized oligonucleotide

<400> SEQUENCE: 6

```
ggacagaucg ccuggagacg ccauccacgc uguuugacc uccauagaag acaccgggac      60
cgauccagcc uccgcggccg ggaacgguc auuggaacgc ggauucccg ugccaagagu      120
gacucaccgu ccuugacacg auggcaacug gaucaagaac cucccuccug cucgcauucg    180
gccugcucug ucucccaugg cuccaagaag gaagcgcguu ccccacuauc ccccucucgg    240
agguucagcu ggucgaaagc ggggcggcc ucguccagcc agguggaucc uccgccuga     300
gcugcgccgc guccggauac acuuucacca acuacggcau gaacuggguc cgccaggcgc   360
cgggaaaggg acuggaaugg gucggcugga ucaauaccua cacuggagag ccuaccuacg   420
ccgcugacuu uaagaggcgg uucacuuucu cacuggauac uuccaaguca accgcuuacc   480
```

| | |
|---|---|
| uucagaugaa uucccugcgc gccgaggaua ccgcagugua uuacugcgcc aaauacccgc | 540 |
| auuacuacgg cuccagccac ugguacuuug acgugugggg ucaaggaacc cuggugacug | 600 |
| ugucguccgc uuccaccaag ggaccaagcg uguuccacu cgccccgagc ucaaaaucga | 660 |
| cgucgggagg uacugccgca cuggggugcu uggucaagga cuacuuucca gagccgguga | 720 |
| cuguuccug gaacagcgga gcgcucaccu cgggcgugca caccuucccu gcggugumugc | 780 |
| agucaucugg acuguacucg cuguccagcg uggucacggu cccgagcucg ucgcucggga | 840 |
| cccaaaccua cauuugcaau gucaaccaca agccaucgaa caccaaaguc gacaagaagg | 900 |
| uggaaccgaa gucgugcgac aagcucauua cgugcccacc guguccggcu ccggaacugu | 960 |
| uggggggccc cuccguguuc cuuuucccgc aaagccuaa ggacacucuc augaucucac | 1020 |
| ggacgccaga agugaccugu guggucgugg augugcaca ugaggauccg gaagucaaau | 1080 |
| ucaacuggua uguggacggg guggaagugc auaaugccaa aaccaaaccu cgcgaggagc | 1140 |
| aguacaacuc aaccuaccgg gugugguccu gcugacugu gcugaccag gacuggcuga | 1200 |
| auggaaagga guacaaaugc aaggucagca acaaggcccu uccgccccca aucgaaaaga | 1260 |
| cgaucucgaa ggccaaaggu cagccgcgag agccucaagu guacacucug ccgccgucaa | 1320 |
| gagaagaaau gacuaagaac caaguuuccc ucacuugccu ggugaagggc uucuacccca | 1380 |
| gcgacaucgc aguggaaugg gagagcaacg gacagccgga aaacaacuau aagaccaccc | 1440 |
| cuccugguguu ggacucggau gguuccuucu uccuuuacag caagcugacc guggauaaau | 1500 |
| cgcgguggca gcaaggaaau guguuuucau gcucagucau gcacgaggcg cugcacaauc | 1560 |
| acuacacuca gaaguccag ucgcugucgc caggaaaaaua acggguggca ucccugugac | 1620 |
| cccuccccag ugccucuccu ggcccuggaa guugccacuc cagugcccac cagccuuguc | 1680 |
| cuaauaaaau uaaguugcau caagcu | 1706 |

<210> SEQ ID NO 7
<211> LENGTH: 744
<212> TYPE: RNA
<213> ORGANISM: Artificial Sequence
<220> FEATURE:
<223> OTHER INFORMATION: chemically synthesized oligonucleotide

<400> SEQUENCE: 7

| | |
|---|---|
| auggccacug gaucaagaac cucacugcug cucgcuuuug acugcuuug ccugcccugg | 60 |
| uugcaagaag gaucggcuuu cccgaccauc ccacucuccg acauucaaau gacgcaguccc | 120 |
| ccaucgagcc cucucagcauc aguggggau cgcugacua ucacuugcuc ggcgagccag | 180 |
| gauaucagca auuaccugaa cugguaucag caaaagccug gaaaggcacc gaaggugcug | 240 |
| aucuacuuca cccucaagccu ccaucggggu gucccguccc gcuucagcgg cuccggcuca | 300 |
| ggcacugacu ucacccugac uaucucccucg cugcaaccgg aagauucgc cacuuacuac | 360 |
| ugucagcagu acuccaccgu gccuuggacg uucggacagg gaaccaaagu ugagauuaag | 420 |
| cggacggucg cggccccuc cguguuuauc uuuccgccuu cggacgagca gcugaagucg | 480 |
| ggaaccgccu cugucgugug ccuccugaac aacuucuacc cgcgggaagc caaggugcag | 540 |
| uggaaagugg auaacgcgcu ucagagcggc aauucgcaag agccgugac cgaagaggac | 600 |
| ucgaaggacu caaccuacuc cccucagcuca acccucacuu ugcgaaggc cgacuacgag | 660 |
| aagcacaaag ucuacgcaug cgaagucacc caccaggguc ugucgagccc agugacuaaa | 720 |
| uccuucaaua gggggggaaug uuaa | 744 |

```
<210> SEQ ID NO 8
<211> LENGTH: 989
<212> TYPE: RNA
<213> ORGANISM: Artificial Sequence
<220> FEATURE:
<223> OTHER INFORMATION: chemically synthesized oligonucleotide

<400> SEQUENCE: 8
ggacagaucg ccuggagacg ccauccacgc uguuuugacc uccauagaag acaccgggac      60
cgauccagcc uccgcggccg ggaacggugc auuggaacgc ggauucccg ugccaagagu     120 gacucaccgu ccuugacacg auggccacug gaucaagaac cucacugcug cucgcuuuug    180
gacugcuuug ccugcccugg uugcaagaag gaucggcuuu cccgaccauc ccacucuccg    240
acauucaaau gacgcagucc ccaucgagcc ucucagcauc aguggggau cgcgugacua     300 ucacuugcuc ggcgagccag gauaucagca auuaccugaa cugguaucag caaaagccug    360
gaaaggcacc gaaggugcug aucuacuuca ccucaagccu ccauucgggu gucccguccc    420
gcuucagcgg uccggcuca ggcacugacu ucacccugac uaucuccucg cugcaaccgg     480
aagauuucgc cacuuacuac ugucagcagu acuccaccgu gccuuggacg uucggacagg    540
gaaccaaagu ugagauuaag cggacggucg cggcccccuc cguguuuauc uuuccgccuu    600
cggacgagca gcugaagucg ggaaccgccu cugucgugug ccuccugaac aacuucuacc    660
cgcgggaagc caaggugcag uggaaagugg auaacgcgcu ucagagcggc aauucgcaag    720
aguccgugac cgaagaggac ucgaaggacu caaccuacuc ccucagcuca acccucacuu    780
ugucgaaggc cgacuacgag aagcacaaag ucuacgcaug cgaagucacc caccagggguc    840 ugucgagccc agugacuaaa uccuucaaua gggggaaug uuaacggug gcaucccugu      900 gaccccuccc cagugccucu ccuggcccug gaaguugcca cuccagugcc caccagccuu    960
guccuaauaa aauuaaguug caucaagcu                                      989

<210> SEQ ID NO 9
<211> LENGTH: 99
<212> TYPE: RNA
<213> ORGANISM: Artificial Sequence
<220> FEATURE:
<223> OTHER INFORMATION: chemically synthesized oligonucleotide

<400> SEQUENCE: 9
auggccacug gaucaagaac cucacugcug cucgcuuuug acugcuuug ccugcccugg      60 uugcaagaag gaucggcuuu cccgaccauc ccacucucc                           99

<210> SEQ ID NO 10
<211> LENGTH: 99
<212> TYPE: RNA
<213> ORGANISM: Artificial Sequence
<220> FEATURE:
<223> OTHER INFORMATION: chemically synthesized oligonucleotide

<400> SEQUENCE: 10
auggcaacug gaucaagaac cucccuccug cucgcauucg gccugcucug ucucccaugg     60
cuccaagaag gaagcgcguu ccccacuauc ccccucucg                           99
```